United States Patent [19]

Okada et al.

[11] Patent Number: 5,538,976
[45] Date of Patent: Jul. 23, 1996

[54] SUBSTITUTED TERTIARY AMINO COMPOUND OR SALT THEREOF

[75] Inventors: Minoru Okada; Toru Yoden; Eiji Kawaminami; Yoshiaki Shimada; Masafumi Kudou; Yasuo Isomura, all of Ibaraki, Japan

[73] Assignee: Yamanouchi Pharmaceutical Co., Ltd., Tokyo, Japan

[21] Appl. No.: 325,383

[22] PCT Filed: Apr. 27, 1993

[86] PCT No.: PCT/JP93/00548

§ 371 Date: Oct. 26, 1994

§ 102(e) Date: Oct. 26, 1994

[87] PCT Pub. No.: WO93/22290

PCT Pub. Date: Nov. 11, 1993

[30] Foreign Application Priority Data

Apr. 28, 1992 [JP] Japan .................... 4-137762
Aug. 10, 1992 [JP] Japan .................... 4-234298

[51] Int. Cl.$^6$ .................. A61K 31/505; C07D 239/42; C07D 237/20
[52] U.S. Cl. .................. 514/256; 514/242; 514/245; 514/252; 544/180; 544/182; 544/194; 544/224; 544/238; 544/322
[58] Field of Search .................. 514/242, 245, 514/252, 256; 544/180, 182, 194, 224, 238, 322, 296

[56] References Cited

U.S. PATENT DOCUMENTS 4,762,836  8/1988  Hirsch .................... 514/357
4,774,251  9/1988  Hirsch et al. .................. 514/357

OTHER PUBLICATIONS

Jones et al. J. Med. Chem., 33, 416–429, 1990.

*Primary Examiner*—Yogendra N. Gupta
*Attorney, Agent, or Firm*—Burgess, Ryan and Wayne

[57] ABSTRACT

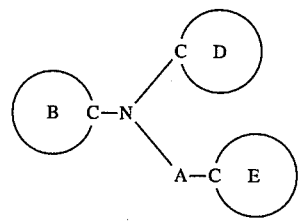

A substituted tertiary amino compound represented by general formula (I) or a pharmaceutically acceptable salt thereof. They have an aromatase inhibiting activity and are useful as a prophylactic and/or therapeutic agent for breast cancer, mastopathy, endometriosis, prostatic-hypertrophy, and so forth.

11 Claims, No Drawings

SUBSTITUTED TERTIARY AMINO COMPOUND OR SALT THEREOF

FIELD OF THE INVENTION

This invention relates to a novel substituted tertiary amino compound or a pharmaceutically acceptable salt thereof having an aromatase inhibiting activity and useful as a drug, a process for preparing the same, and a pharmaceutical composition containing the same.

BACKGROUND ART

It is known that an enzyme, aromatase, takes part in the final stage of biosynthesis of estrogen. Aromatase aromatizes the ring A of the steroid and uses androgen as a substrate to produce an estrogen. Inhibition of the aromatase activity leads to prevention and treatment of various diseases in which an estrogen participates as an exacerbating factor.

Several aromatase inhibiting compounds have hitherto been proposed based on the above concept. Typical examples of known aromatase inhibiting compounds include imidazolyl-, triazolyl-, pyridyl- or pyrimidyl-substituted methyl compounds disclosed in EP-B-236940, EP-B-293978, U.S. Pat. No. 4,762,836, and *J. Med. Chem.*, Vol. 33, p. 416 (1990).

Further, U.S. Pat. No. 4,774,251 describes that a compound having a pyridyl- or pyrazyl-substituted tertiary amino group and one or two phenyl groups, as represented by the following general formula, exhibits an aromatase inhibiting activity.

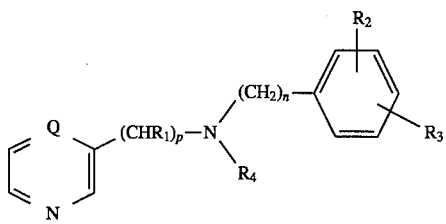

(cf. U.S. Pat. No. 4,774,251 as to definitions of the symbols)

The compound according to the present invention is distinctly different in structure from any of the compounds found in the above-described literature in that it contains a pyrimidine ring, a pyridazine ring or a triazine ring as a basic structure.

Additionally, the compound of the present invention has been proved highly useful as it has 100 times or more the aromatase inhibiting activity of the compound disclosed in the literature.

DISCLOSURE OF THE INVENTION

The substituted tertiary amino compound of the present invention is represented by the general formula (I):

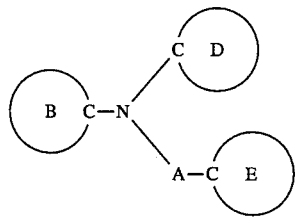

wherein A represents a single bond, a lower alkylene group or a group represented by formula:

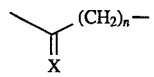

wherein n represents an integer of from 1 to 6, and X represents an oxygen atom, a sulfur atom or a group represented by formula: CH$_2$;

ring B represents a pyrimidine ring, a pyridazine ring or a triazine ring;

and rings D and E, which may be the same or different, each represent a substituted or unsubstituted aryl group, a substituted or unsubstituted 5- or 6-membered heterocyclic group containing 1 to 3 hetero atoms each selected from a nitrogen atom, an oxygen atom, and a sulfur atom, or a substituted or unsubstituted bicyclic condensed heterocyclic group consisting of the above heterocyclic group condensed with a benzene ring; provided that where rings D and E both represent a benzene ring, at least one of them has a substituent.

The compound of the present invention will further be explained. The term "lower" as used in definitions of general formulae in this specification means a straight or branched carbon chain having from 1 to 6 carbon atoms unless otherwise noted.

Accordingly, a "lower alkyl group" as one of the substituents on ring D or E may include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, and a 1-ethyl-2-methylpropyl group.

The "lower alkylene group" is a straight or branched carbon chain having from 1 to 6 carbon atoms and includes a methylene group, an ethylene group, a propylene group, a tetramethylene group, a 2-methyltrimethylene group, a 1-ethylethylene group, a pentamethylene group, and a 1,2-diethylethylene group, with a methylene group and an ethylene group being preferred.

The "aryl group" which constitutes the "substituted or unsubstituted aryl group" represented by ring D or E includes a phenyl group, a naphthyl group, an anthracenyl group, and a phenanthrenyl group. The "5- or 6-membered heterocyclic group containing 1 to 3 hetero atoms each selected from a nitrogen atom, an oxygen atom, and a sulfur atom" which constitutes the "substituted or unsubstituted 5or 6-membered heterocyclic group containing 1 to 3 hetero atoms each selected from a nitrogen atom, an oxygen atom, and a sulfur atom" includes a furyl group, a thienyl group, a thiazolyl group, a thiadiazolyl group, an oxazolyl group, an imidazolyl group, a triazolyl group, a pyrrolyl group, a pyridyl group, a pyrimidinyl group, and a pirazinyl group. The "bicyclic condensed heterocyclic group consisting of the above heterocyclic group condensed with a benzene ring" which constitutes in the "substituted or unsubstituted bicyclic condensed heterocyclic group consisting of the above heterocyclic group condensed with a benzene ring" includes a heterocyclic residue of benzothiazole, benzoxazole, quinoline, isoquinoline, benzotriazole or benzofurazane.

As previously stated., the "aryl group", "5- or 6membered heterocyclic group containing 1 to 3 hetero atoms each selected from a nitrogen atom, an oxygen atom, and a sulfur atom", and "bicyclic condensed heterocyclic group consisting of the above heterocyclic group condensed with a benzene ring" may contain one or more, preferably 1 or 2, substituents.

Such substituents include a halogen atom, a cyano group, a cyano-lower alkyl group, a nitro group, a trifluoromethyl group, a hydroxyl group, an amino group, a mono- or di-lower alkylamino group, a lower alkyl group, a lower alkoxy group, a carboxyl group, a lower alkoxycarbonyl group, a lower alkanoyl group, a lower alkanoyloxy group, a lower alkanoylamino group, an aroyl group, an aroyloxy group, a carbamoyl group, a mono- or di-lower alkylaminocarbonyl group, a sulfonic acid group, a lower alkylsulfonyl group, a sulfamoyl group, and a mono- or di-lower alkylsulfamoyl group. Preferred of them are a halogen atom, a cyano group, a cyano-lower alkyl group, a nitro group, a trifluoromethyl group, a hydroxyl group, an amino group, a lower alkyl group, a lower alkylsulfonyl group, a lower alkoxy group, a carboxyl group, a lower alkoxycarbonyl group, a lower alkanoyl group, and a lower alkanoylamino group. More preferred are a halogen atom, a cyano group, and a nitro group.

The "halogen atom" as used herein includes a fluorine atom, a chlorine atom, a bromine atom, and an iodine atom. The "lower alkoxy group" includes a methoxy group, an ethoxy group, a propoxy group, an isopropoxy group, a butoxy group, an isobutoxy group, a sec-butoxy group, a tert-butoxy group, a pentyloxy(amyloxy) group, an isopentyloxy group, a tert-pentyloxy group, a neopentyloxy group, a 2-methylbutoxy group, a 1,2-dimethylpropoxy group, a 1-ethylpropoxy group, and a hexyloxy group, with a methoxy group and an ethoxy group being preferred.

The "lower alkoxycarbonyl group" includes a methoxycarbonyl group, an ethoxycarbonyl group, a propoxycarbonyl group, a butoxycarbonyl group, a tert-butoxycarbonyl group, and a pentyloxycarbonyl group. The "lower alkanoyl(oxy) group" includes an acetyl(oxy) group, a propionyl(oxy) group, a butyryl(oxy) group, a valeryl(oxy) group, and an isovaleryl(oxy) group. The "lower alkanoylamino group" includes an acetylamino group, a propionylamino group, a butyrylamino group, a valerylamino group, and an isovalerylamino group.

The "aroyl group" or "aroyloxy group" includes a benzoyl(oxy) group, a 1-naphthylcarbonyl(oxy) group, a 2-naphthylcarbonyl(oxy) group, a thienoyl(oxy) group, a pyrroloyl(oxy) group, and a 2-, 3- or 4-pyridylcarbonyl(oxy) group.

The "lower alkyl group" in the "mono- or di-lower alkylaminocarbonyl group" or "mono- or di-lower alkylsulfamoyl group" includes those described above. Typical examples of the "mono- or di-lower alkylaminocarbonyl group" or "mono- or di-lower alkylsulfamoyl group" include a methylaminocarbonyl group, a dimethylaminocarbonyl group, a diethylaminocarbonyl group, a propylaminocarbonyl group, a methylsulfamoyl group, a dimethylsulfamoyl group, and a diethylaminosulfamoyl group.

The "lower alkylsulfonyl group" includes a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, and a hexylsulfonyl group.

The compound of the present invention can easily form a salt with an inorganic acid or an organic acid, and these salts have an aromatase inhibiting activity similarly to the free bases. Suitable salts include inorganic acid salts, such as a hydrochloride, a hydrobromide, a sulfate, a nitrate, and a phosphate; and organic acid salts, such as an oxalate, a fumarate, and a tartrate.

Depending on the kind of the substituent, the compound of the present invention can also form a pharmaceutically acceptable salt with an alkali metal or an alkaline earth metal (e.g., sodium, potassium, magnesium or calcium) or an organic amine, such as ammonia or triethylamine.

The compound of the present invention may have an asymmetric carbon atom depending on the kind of the substituent. The compound of the present invention includes all the isomers based on the asymmetric carbon atom, such as optical isomers (e.g., diastereomers and optically active compounds).

The compound of the present invention sometimes takes the form of various hydrates, solyates, tautomers, and the like. The compound of the present invention includes all of these compounds, either isolated or mixed.

The compound of the present invention can be prepared through a variety of processes taking advantage of the characteristics of the basic skeleton or the substituents. Typical processes are shown below.

Process 1:

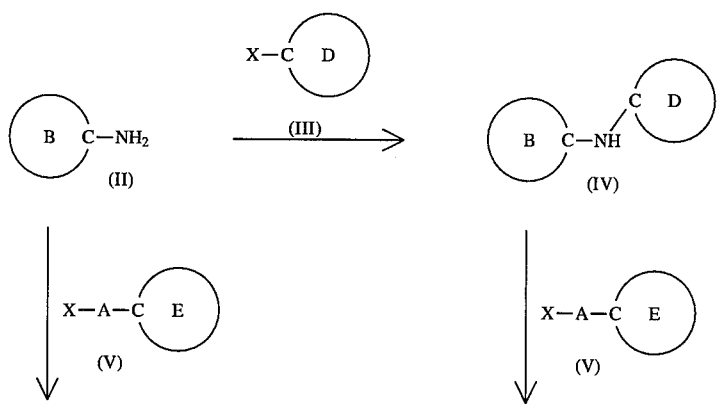

-continued
Process 1:

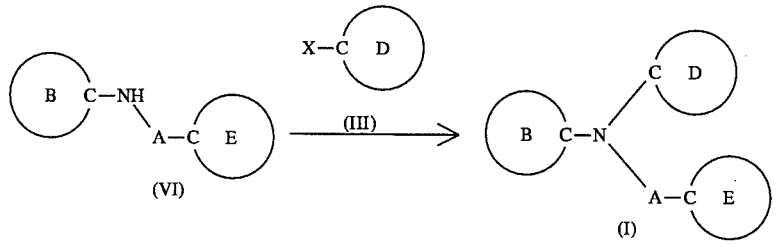

wherein X represents a halogen atom, an arylsulfonyloxy group, a lower alkylsulfonyloxy group, etc. (the same definition applies hereinafter).

The desired compound (I) can be prepared from the starting compound (II) through two pathways as shown above. Each reaction step involved in the two pathways is an alkylation reaction or an acylation reaction of an amino group, which can be carried out in the same manner.

That is, the above reaction can be carried out by bringing reaction-corresponding amounts of the starting compounds into contact with each other in a solvent inert to the reaction, such as dimethylformamide, dimethyl sulfoxide, tetrahydrofuran, dimethoxyethane, acetone, or methyl ethyl ketone, in the presence of a base. Useful bases include sodium hydride, sodium amide, n-butyl lithium, potassium t-butoxide, metallic sodium, sodium methoxide, sodium ethoxide, sodium hydroxide, and potassium hydroxide. The reaction can be effected easily at room temperature.

In this case, the arylsulfonyloxy group includes a phenylsulfonyloxy group and a p-toluenesulfonyloxy group, and the lower alkylsulfonyloxy group includes a sulfonyloxy group substituted with a lower alkyl group such as a methylsulfonyloxy group, an ethylsulfonyloxy group, and a propylsulfonyloxy group.

Process 2:

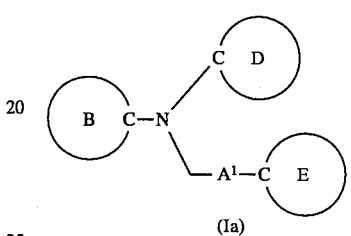

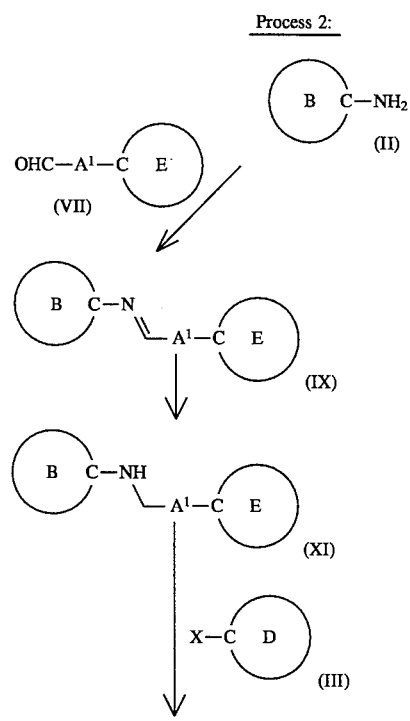

-continued
Process 2:

wherein $A^1$ represents a lower alkylene group having less methylene groups than A by one (the same definition applies hereinafter).

According to this process, an amino compound (II) and an aldehyde compound (VII) are reacted to form a corresponding Schiff base (IX), the Schiff base (IX) is reduced to obtain a compound (XI), and the compound (XI) is alkylated or acylated in the same manner as in process 1 to obtain the desired compound (Ia). The reaction for forming a Schiff base can be carried out by, for example, an azeotropic dehydration reaction in a solvent, such as an alcohol (e.g., methanol or ethanol), benzene or toluene, in the presence of an acid catalyst. The reduction reaction can be performed in a conventional manner, for example, by using sodium borohydride, lithium borohydride, sodium cyanoborohydride, etc. The reaction solvent to be used includes alcohols, such as methanol and ethanol, organic solvents, such as acetic acid, water, and mixtures thereof. In the reaction, the Schiff base to be reduced may not be isolated, and the reduction may be effected by adding a reducing agent to the reaction mixture containing the Schiff base.

Process 3:

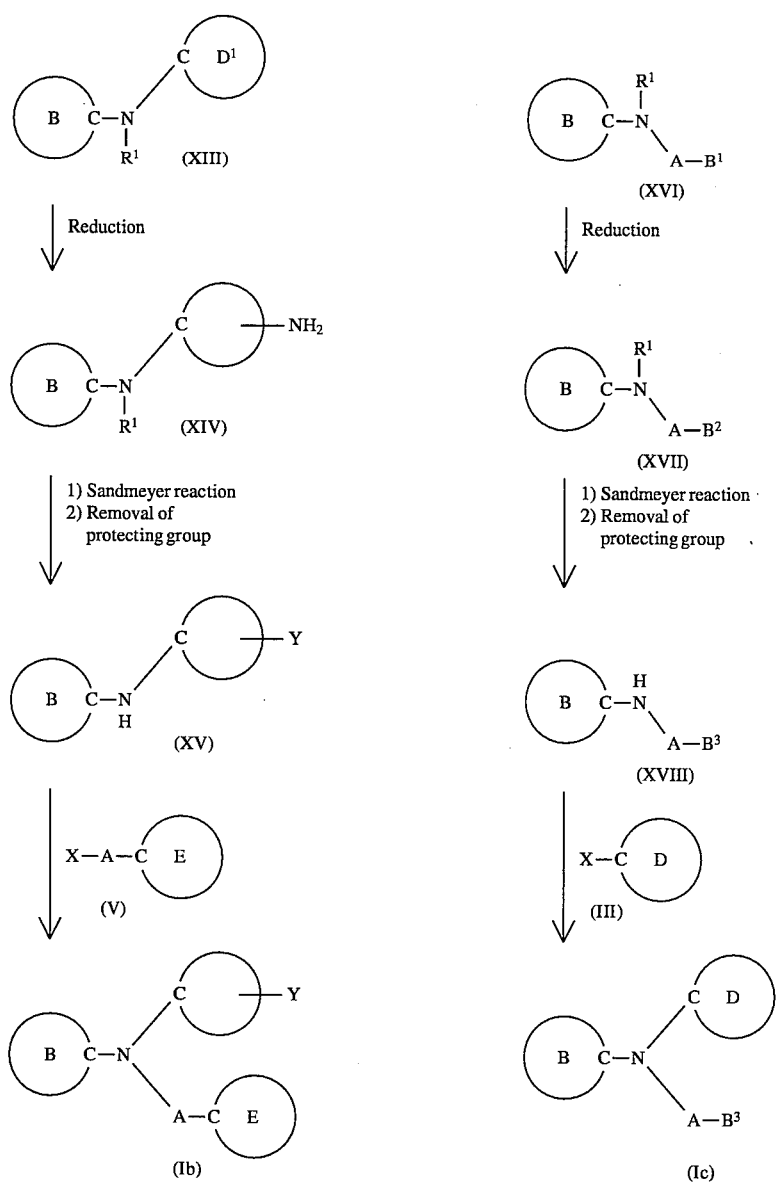

wherein $R^1$ represents an amino-protecting group; Y represents a halogen atom; $B^1$ and $D^1$ each represent an aryl group, a 5- or 6-membered heterocyclic ring or a bicyclic condensed heterocyclic ring composed of the above heterocyclic ring condensed with a benzene ring, each of which is substituted with a nitro group; $B^2$ represents an aryl group, a 5- or 6-membered heterocyclic ring or a bicyclic condensed heterocyclic ring composed of the above heterocyclic ring condensed with a benzene ring, each of which is substituted with an amino group; and $B^2$ represents an aryl group, a 5- or 6-membered heterocyclic ring or a bicyclic condensed heterocyclic ring composed of the above heterocyclic ring condensed with a benzene ring, each of which is substituted with a halogen atom (the same definitions apply hereinafter).

According to this process, a halogen-substituted compound of the present invention represented by the general formula (Ib) or (Ic) is obtained.

That is, a compound represented by the general formula (XIII) or (XVI) is reduced to an amino compound represented by the general formula (XIV) or (XVII), which is then subjected to the Sandmeyer reaction to introduce a halogen atom. The protecting group is removed to obtain a compound represented by the general formula (XV) or (XVIII), and the resulting compound is reacted with a compound represented by the general formula (V) or (III) to obtain a desired compound. The reduction of the compound represented by the general formula (XIII) can be carried out in a conventional manner, for example, by chemical reduction or catalytic reduction.

Suitable reducing agents to be used for chemical reduction include metals, such as tin, zinc and iron. Catalytic reduction is carried out in the presence of a commonly employed catalyst, such as a platinum catalyst, e.g., platinum or platinum oxide, a palladium catalyst, e.g., palladium black or palladium oxide, or a nickel catalyst, e.g., Raney nickel.

Commonly employed solvents, such as methanol, ethanol, propanol, ethyl acetate, and acetic acid can be used for the reduction. The protecting group available for the nitrogen atom of the compound represented by the general formula (XIII) or (XVI) is a common protective acyl group, such as an acetyl group or a benzoyl group. The protecting group can be introduced by reacting a starting compound with acetic anhydride, acetyl chloride, benzoyl chloride, etc. in the presence of a base, such as sodium acetate, pyridine, picoline, lutidine, trimethylamine or triethylamine. This reaction may be effected with a solvent such as dichloromethane, dichloroethane, chloroform, benzene or toluene, or without a solvent.

The compound (XIV) or (XVII) thus obtained is then subjected to the Sandmeyer reaction to introduce a halogen atom, and the protecting group is removed to obtain the compound (XV) or (XVIII). The Sandmeyer reaction can be carried out in a usual manner by using cuprous chloride, cuprous bromide or cuprous iodide in combination with hydrochloric acid, hydrobromic acid, hydroiodic acid, sulfuric acid, etc. in a solvent, such as water, acetone, dioxane or tetrahydrofuran. Removal of the protecting group is effected by acid hydrolysis using dilute hydrochloric acid, dilute sulfuric acid, etc. The reaction of compound (XV) thus obtained with compound (V) or (III) can be performed according to the method described in processes 1 and 2.

Other Processes:

1) A compound of the present invention having an amino group as a substituent can be obtained by reducing a compound of the present invention having a corresponding nitro group. This reaction is a substituent conversion reaction, and the reduction reaction adopted in process 3 can be applied.

2) A compound of the present invention having a lower alkanoylamino group as a substituent can be obtained by reacting a compound of the present invention having a corresponding amino group with acetic anhydride, etc. in a usual manner.

3) A compound of the present invention having a benzotriazolyl group as a substituent can be obtained by reducing a compound having an amino group (or a mono-substituted amino group) and a nitro group as adjacent substituents on the phenyl group to convert the nitro group to an amino group, and reacting the resulting compound with sodium nitrite, potassium nitrite, etc. to effect cyclization.

The thus prepared compound of the present invention is isolated and purified in a known manner, such as extraction, precipitation, fractional chromatography, fractional crystallization, recrystallization or the like means. The compound of the present invention can be led to a desired salt by a conventional salt formation reaction.

INDUSTRIAL APPLICABILITY

The compound of the present invention has an inhibiting action on aromatase, an enzyme having aromatizing activity which participates in biosynthesis of estrogen from androgen. Therefore, the compound of the present invention is useful as a preventing and/or treating agent for various diseases in which estrogen is participated as an exacerbating factor, such as breast cancer, mastopathy, endometriosis, prostatic hypertrophy, hysteromyoma, cancer of uterine body, and the like. [cf. *Pharmacia*, Vol. 26, No. 6, p. 558 (1990); *Clinical Endocrinology*, Vol. 32, p. 623 (1990); *J. Steroid Biochem. Molec. Biol.*, Vol. 37, No. 3, p. 335 (1990); *Br. J. Cancer*, Vol. 60, p. 5 (1989); *Endocrinology*, Vol. 126, No. 6, p. 3263 (1990); *The Journal of Pharmacology and Experimental Therapeutics*, Vol. 244, No. 2 (1988); *Endocrinal, Japan*, Vol. 37, No. 5, p. 719 (1990); and *Steroids*, Vol. 50, p. 1 (1987)].

Method of Experimentation:

The pharmacological effects of the compound of the present invention were determined as follows.
(1) Experimentation in animal (rats):
(a) Inhibiting activity on aromatase of rat ovary origin:

Measured in accordance with the method described in *J. Biol. Chem.*, Vol. 249, p. 5364 (1974). $IC_{50}$ of a test compound in aromatase inhibition was obtained from inhibition of $^3H_2O$ released from [1,2-$^3$H]-androstenedione in the microsome of a rat ovary.
(b) In vivo inhibiting activity on estrogen production in rat:

PMSG (pregnant mare serum gonadotropin) (100 IU/rat) was subcutaneously injected to an immature female Wister rat weighing 60 g. After 72 hours from the injection, a suspension of a test compound in 0.5 ml of 20% polyethylene glycol aqueous solution was given to the rat per os. A 20% polyethylene glycol aqueous solution was administered to a control group. After 3 hours from the administration of the drug or placebo, the rat was decapitated and bled out, and the ovary was removed. The estradiol concentration in the ovary was measured by RIA.
(c) Antitumor activity in rat:

The antitumor activity on breast carcinoma was measured in a dimethylbenzanthracene (DMBA)-induced tumor in a female Sprague-Dawlay rat.

This experimentation is commonly employed as a method for determining an antitumor activity in an animal model of breast carcinoma.
(2) Experimentation using aromatase of human origin:
(a) Inhibiting activity on aromatase of human placenta origin:

Measured in accordance with the method described in *Endocrine Research*, Vol. 16, No. 2, p. 253 (1990).

The inhibiting activity of a test compound was obtained from inhibition of $^3H_2O$ released from [1,2-$^3$H]androstenedione in the microsome of a human placenta.

Results of Experimentation:

The results obtained are shown below. 1. In vitro inhibiting activity on aromatase in microsome of rat ovary:

$IC_{50}$ value of a test compound for in vitro aromatase inhibition in the microsome of a rat ovary was obtained by the method described in (1)-(a) above. The results obtained are shown in the following table.

| Test Compound | Concentration for 50% Inhibition on Aromatase Activity |
| --- | --- |
| Compound of Invention (Example 34) | $IC_{50} = 0.22$ nM |
| Comparative Compound 1 | $EC_{50} = 55$ nM |
| Comparative Compound 2 | $EC_{50} < 50$ nM |

Note: 1) $IC_{50}$ and $EC_{50}$ are used for the same meaning, referring to a drug concentration at which an aromatase activity is 50% inhibited.

2) Comparative Compound 1:

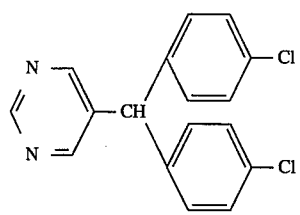

[the compound disclosed in U.S. Pat. No. 4,762,836, Table 1 (27th compound) and in *J. Med. Chem.*, Vol. 33, p. 416 (1990), Table IV (29th compound); Development No.: LY56110]

3) Comparative Compound 2:

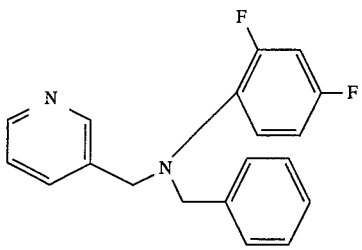

[the compound disclosed in U.S. Pat. No. 4,774,251, Table 1 (11th compound)]

The above-described comparative compounds are the most potent in aromatase inhibition among the compounds disclosed in U.S. Pat. Nos. 4,762,836 and 4,774,251, respectively. Compared with these compounds, the compound according to the present invention exhibited significantly more potent activity.

2. In vivo inhibiting activity on estrogen production in rat:

In the measurement of in vivo inhibiting activity on estrogen production in rats according to the above method (1)-(b), the compound of the present invention (Example 34) at a dose of 0.03 mg/kg showed 86% inhibition on estradiol biosynthesis with respect to the control. It has now been proved that the compound of the present invention also exhibits a very effective activity based on aromatase inhibition in in vivo experimentation.

3. Antitumor activity in rat:

As a result of the experimentation according to the method (1)-(c), it was found that the compound of the present invention (Example 34), when orally given to rats bearing breast carcinoma at a daily dose of from 0.04 to 1.0 mg/kg for 2 weeks, caused suppression or regression of tumors in the mammary gland, etc.

These results suggest the possibility that the compound of the present invention is also effective in human diseases, such as breast carcinoma.

4. In vitro inhibiting activity on aromatase in microsome of human placenta:

$IC_{50}$ value for in vitro aromatase inhibition in the microsome of a human placenta was obtained according to the method (2)-(a). The result obtained is shown in the following table.

| Test Compound | $IC_{50}$ |
|---|---|
| Compound of Invention (Example 34) | 0.036 nM |

As is obvious from the above result, the compound of the present invention exhibited very potent in vitro aromatase inhibition activity in the microsome of a human placenta.

Other Considerations:

Steroid hormones other than estrogen include aldosterone, cortisol, testosterone, and so forth, and it has been known that these steroid hormones have various extremely important physiological activities.

Therefore, it is considered that, if the compound of the present invention inhibits production of steroid hormones other than estrogen, it unavoidably results in development of side effects. Hence, the following study was conducted.

Influences on Production of Hormones other than Estrogen:

The compound of the present invention showed no substantial inhibitory activity in each of an in vivo and in vitro test of androsterone production inhibition, an in vivo and in vitro test of cortisol production inhibition, and an in vitro test of testosterone production inhibition.

The compound of the present invention is a selective aromatase inhibiting agent having substantially no influence on steroid hormones other than estrogen and is therefore expected to be a compound having high safety with little side effects.

Further, as a result of investigations into the behavior of the compound of the present invention in a living body, it has been revealed that the compound is long-acting and thus has a favorable profile as a drug.

The compound represented by the general formula (I), a non-toxic salt thereof, or a hydrate thereof is usually administered orally or parenterally for the above-mentioned purposes. While varying depending on the age, body weight, symptoms, therapeutic effects, administration route, treatment period, and the like, the dose usually ranges from 0.1 to 100 mg/day, preferably from 1 to 10 mg/day, for an adult in a single or several divided doses for oral administration, or from 0.1 to 100 mg/day for an adult in a single or several divided doses for parenteral administration or continuous intravenous injection for 1 to 24 hours per day. Since the dose is subject to variation depending on various conditions, sufficient efficacy may sometimes be achieved with a lower dose.

Solid compositions for oral administration include tablets, powders, granules, and the like. Such solid preparations comprise a mixture of at least one active ingredient with at least one inert diluent, such as lactose, mannitol, glucose, hydroxypropyl cellulose, microcrystalline cellulose, starch, polyvinyl pyrrolidone, magnesium aluminate metasilicate, etc. The compositions may further contain conventional additives other than the inert diluents, for example, lubricants, such as magnesium stearate; disintegrators, such as calcium carboxymethylcellulose; stabilizers, such as lactose; and dissolution assistants, such as glutamic acid and aspartic acid. If desired, tablets or pills may have a gastric or enteric coat of sucrose, gelatin, hydroxypropylcellulose, hydroxypropylmethylcellulose phthalate, etc.

Liquid compositions for oral administration include pharmaceutically acceptable emulsions, solutions, suspensions, syrups, and elixirs. The liquid compositions contain generally employed inert diluents, such as purified water and ethanol. The liquid compositions may further contain, in addition to the inert diluents, other auxiliary agents, such as wetting agents and suspending agents, sweeteners, flavors, aromatics, and antiseptics.

Injectable solutions for parenteral administration include sterile aqueous or non-aqueous solutions, suspensions and emulsions. The aqueous solutions and suspensions include injectable distilled water and physiological saline. The non-aqueous solutions and suspensions include propylene glycol, polyethylene glycol, vegetable oils, such as olive oil, alcohols, e.g., ethanol, and Polysorbate 80, and the like. These compositions may further contain adjuvants, such as antiseptics, wetting agents, emulsifying agents, dispersants, stabilizers (e.g., lactose), and dissolution assistants (e.g., glutamic acid and aspartic acid). The liquids are sterilized by, for example, filtration through a bacteria-trapping filter, addition of a bactericide, or irradiation. Injectable solutions may also be prepared by preparing a sterile solid composition and dissolving it in sterile water or a sterile injectable solvent on use.

BEST MODE FOR CARRYING OUT THE INVENTION

The present invention will be illustrated in greater detail with reference to Examples. The process for preparing the starting compounds used in the Examples are explained by way of Reference Examples.

REFERENCE EXAMPLE 1

To 20 ml of dimethyl sulfoxide was added 2.8 g of potassium tert-butoxide. After stirring at room temperature for 30 minutes, 1.9 g of 5-aminopyrimidine was added thereto, followed by stirring at room temperature for 30 minutes. To the solution was added 1.21 g of 4-fluorobenzonitrile, and the mixture was stirred at room temperature for 30 minutes and then at 50° C. for 30 minutes. The reaction mixture was poured into ice-water, neutralized with hydrochloric acid. The resulting crystals were collected by filtration and dissolved in acetone. Any insoluble matter was removed by filtration, and the solvent was removed by distillation. The resulting crystals were washed with ethyl ether to obtain 1.04 g of 5-[(4-cyanophenyl)amino]pyrimidine.

Mass Spectrum (m/z): 196 ($M^+$)

NMR Spectrum (DMSO-$d_6$, TMS internal standard) δ: 7.19 (2 H, d, J=9 Hz), 7.68 (2 H, d, J=9 Hz), 8.70 (2 H, s), 8.82 (1 H, s), 9.16 (1 H, brs).

The compound of Reference Example 2 was obtained in the same manner as in Reference Example 1.

REFERENCE EXAMPLE 2

5-[(4-Nitrophenyl)amino]pyrimidine

Starting compounds: 5-aminopyrimidine and 4-bromofluorobenzene

NMR Spectrum (DMSO-$d_6$, TMS internal standard) δ: 7.20 (2 H, d, J=9 Hz), 8.14 (2 H, d, J=9 Hz), 8.76 (2 H, s), 8.80 (1 H, s), 9.54 (1 H, brs)

The compounds of Reference Examples 3 to 6 were obtained in the same manner as in Reference Example 1.

REFERENCE EXAMPLE 3

3[(Cyanophenyl)amino]pyridazine

Starting compounds: 3-aminopyridazine and 4-fluorobenzonitrile

MS Spectrum (m/z): 195 ($M^{30}-1$)

NMR Spectrum (DMSO-$d_6$, TMS internal standard) δ: 7.23 (1 H, dd, J=9 Hz, 1 Hz), 7.55 (1 H, dd, J=9 Hz, 1 Hz), 7.75 (2 H, d, J=9 Hz), 7.98 (2 H, d, J=9 Hz), 8.78 (1 H, dd, J=5 Hz, 1 Hz), 9.86 (1 H, br)

REFERENCE EXAMPLE 4

2-[(4-Cyanophenyl)amino]-1,2,4-triazine

Starting compounds: 2-amino-1,2,4-triazine and 4-fluorobenzonitrile

NMR Spectrum (DMSO-$d_6$, TMS internal standard) δ: 7.78 (2 H, d, J=9 Hz), 8.00 (2 H, d, J=9 Hz), 8.58 (1 H, d, J=2 Hz), 8.96 (1 H, d, J=2 Hz)

REFERENCE EXAMPLE 5

4'-(Pyrimidin-5-ylamino)acetophenone

Starting compounds: 5-aminopyrimidine and 4-fluoroacetophenone

NMR Spectrum (DMSO-$d_6$, TMS internal standard) δ: 3.49 (3 H, s), 7.16 (2 H, d, J=9 Hz), 7.89 (2 H, d, J=9 Hz), 8.70 (2 H, s), 8.79 (1 H, s), 9.10 (1 H, br)

REFERENCE EXAMPLE 6

5-[(4-Methanesulfonylphenyl)amino]pyrimidine

Starting compounds: 5-aminopyrimidine and 4-fluoromethanesulfonylbenzene

NMR Spectrum (DMSO, TMS internal standard) δ: 3.14 (3 H, s), 7.25 (2 H, d, J=9 Hz), 7.77 (2 H, d, J=9 Hz), 8.71 (2 H, s), 8.82 (2 H, s), 9.16 (1 H, s)

REFERENCE EXAMPLE 7

To 20 ml of dimethyl sulfoxide was added 2.81 g (25.0 mmol) of potassium tert-butoxide, and to the solution was added 1.90 g (20.0 mmol) of 5-aminopyrimidine at room temperature. After stirring at room temperature for 30 minutes, 1.38 g (10.0 mmol) of 5-fluororobenzofurazan was added thereto, followed by stirring at 50° C. for 2 hours. The reaction mixture was poured into ice-water, adjusted to pH 7.0 with 1 N hydrochloric acid, and filtered. The resulting residue was dissolved in acetone. The acetone solution was filtered, and the filtrate was dried over anhydrous magnesium sulfate. The solvent was removed by distillation under reduced pressure. The residue was purified by silica gel column chromatography (eluted with chloroform-methanol) and then recrystallized from a mixed solvent of chloroform and n-hexane to obtain 0.603 g (2.82 mmol) of 5-[N-(5-pyrimidyl)amino]benzofurazan.

Mass Spectrum (m/z): 213 ($M^+$)

NMR Spectrum (DMSO-$d_6$, TMS internal standard) δ: 7.20 (1 H, dd, J=2 Hz, 1 Hz), 7.41 (1 H, dd, J=10 Hz, 2 Hz), 7.98 (1 H, dd, J=10 Hz, 1 Hz), 8.83 (2 H, s), 8.90 (1 H, s), 9.32 (1 H, s),

REFERENCE EXAMPLE 8

To 7 ml of dimethyl sulfoxide was added 0.69 g (6.15 mmol) of potassium tert-butoxide, and 468 mg (4.92 mmol) of 5-aminopyrimidine was added to the solution while cooling with water. After stirring at room temperature for 1 hour, 500 mg (2.46 mmol) of 2-bromo-5-nitropyridine was added thereto under cooling with water, followed by further stirring at room temperature for 30 minutes. The reaction solution was poured into ice-water and extracted with ethyl acetate. The organic layer was washed with 1 N hydrochloric acid, and the washing was adjusted to pH 8.5 with a 1 N sodium hydroxide aqueous solution and again extracted with ethyl acetate. The organic layer was combined with the above obtained organic layer, washed successively with water and a saturated sodium chloride aqueous solution, and dried over magnesium sulfate. The solvent was removed by distillation under reduced pressure, and the residue was purified by silica gel column chromatography (eluting solvent: chloroform-methanol). The resulting crude crystals were washed with ethyl ether to obtain 0.32 g (1.47 mmol) of 5-[N-(5-nitro-2-pyridyl)amino]pyrimidine.

Mass Spectrum (m/z): 216 (M-H)$^+$

NMR Spectrum (DMSO-$d_6$, TMS internal standard) δ: 7.00 (1 H, d, J=9 Hz), 8.39 (1 H, dd, J=9 Hz, 3 Hz), 8.87 (1 H, s), 9.09 (1 H, d, J=3 Hz), 9.17 (2 H, s), 10.41 (1 H, s)

REFERENCE EXAMPLE 9

To 10 ml of dimethyl sulfoxide was added 1.40 g (12.5 mmol) of potassium tert-butoxide, and to the solution was added 951 mg (10.0 mmol) of 5-aminopyrimidine while cooling with water. After stirring at room temperature for 1 hour, 0.54 ml (5.0 mmol) of 2-fluorobenzonitrile was added thereto while cooling with water, and the mixture was stirred at room temperature for 30 minutes. The reaction mixture was poured into ice-water, and the mixture was adjusted to pH 7.0 with 1 N hydrochloric acid, and filtered. The filter residue was dissolved in 200 ml of acetone, and the acetone solution was filtered. The filtrate was dried over magnesium sulfate, and the solvent was removed by distillation under reduced pressure to obtain 0.53 g (2.70 mmol) of 5-[N-(2cyanophenyl)amino]pyrimidine.

Mass Spectrum (m/z): 196 (M$^+$)

NMR Spectrum (DMSO-$d_6$, TMS internal standard) δ: 7.12 (1 H, t, J=7 Hz), 7.35 (1 H, d, J=8 Hz), 7.57–7.60 (1 H, m), 7.76 (1 H, dd, J=8 Hz, 1 Hz), 8.61 (2 H, s), 8.78 (1 H, s), 8.84 (1 H, s)

REFERENCE EXAMPLE 10

To 5 ml of dimethyl sulfoxide (DMSO) containing 0.34 g of potassium tert-butoxide was added 0.29 g of 5-aminopyrimidine, followed by stirring at room temperature for about 15 minutes. To the reaction mixture was added dropwise 1 ml of a DMSO solution containing 0.33 g of p-fluorobenzotrifluoride, followed by heating at 60° C. for about 40 minutes. The reaction mixture was allowed to cool and poured into 150 ml of ice-water. The thus formed white crystals were collected by filtration and dried to obtain 0.17 g of 5-(4-trifluoromethylphenyl)aminopyrimidine.

Mass Spectrum (m/z): 239 (M$^+$)

NMR Spectrum (DMSO-$d_6$, TMS internal standard) δ: 7.25 (2 H, d, J=8 Hz), 7.59 (2 H, d, J=8 Hz), 8.68 (2 H, s), 8.77 (1 H, s), 9.02 (1 H, s)

EXAMPLE 1

To a suspension of 40 mg of sodium hydride in 2 ml of N,N-dimethylformamide was added 0.22 g of 5-[(4-nitrophenyl)amino]pyrimidine in small portions. After stirring at room temperature for 30 minutes, 0.24 g of 4-trifluoromethylbenzyl bromide was added thereto, followed by stirring at room temperature for 2 hours. The solvent was distilled off under reduced pressure, water was added to the residue, and the mixture was extracted with chloroform. The chloroform layer was washed with water and dried over anhydrous magnesium sulfate. The solvent was distilled off, and the residue was purified by silica gel column chromatography to recover crude crystals from the chloroform eluate. Recrystallization of the crude crystals from a mixed solvent of ethyl acetate and ethyl ether yielded 0.19 g of 5-[N-(4-nitrophenyl)-N-(4trifluoromethylbenzyl)amino]pyrimidine.

| Elemental Analysis (for $C_{18}H_{13}N_4F_3O_2$): | | | | |
|---|---|---|---|---|
| | C (%) | H (%) | N (%) | F (%) |
| Calcd. | 57.76 | 3.50 | 14.97 | 15.23 |
| Found | 57.71 | 3.48 | 14.96 | 15.10 |

NMR Spectrum (CDCl$_3$, TMS internal standard) δ: 5.14 (2H, s), 6.92 (2 H, d, J=9 Hz), 7.40 (2 H, d, J=8 Hz), 7.64 (2 H, d, J=8 Hz), 8.14 (2 H, d, J=9 Hz); 8.70 (2 H, s), 9.07 (1 H, s)

The compounds of Examples 2 to 25 were obtained in the same manner as in Example 1.

EXAMPLE 2

5-[N-(4-Bromobenzyl)-N-(4-nitrophenyl)amino]pyrimidine

Starting compounds: 5-[(4-nitrophenyl)amino]pyrimidine and 4-nitrobenzyl bromide

| Elemental Analysis (for $C_{17}H_{13}N_4BrO_2$): | | | | |
|---|---|---|---|---|
| | C (%) | H (%) | N (%) | Br (%) |
| Calcd. | 53.01 | 3.40 | 14.54 | 20.74 |
| Found | 52.90 | 3.35 | 14.48 | 20.74 |

NMR Spectrum (CDCl$_3$, TMS internal standard) 67: 5.04 (2 H, s), 6.94 (2 H, d, J=9 Hz), 7.16 (2 H, d, J=9 Hz), 7.52 (2 H, d, J=9 Hz), 8.14 (2 H, d, J=9 Hz), 8.72 (2 H, brs), 9.09 (1 H, s)

EXAMPLE 3

5-[N-(4-Nitrobenzyl)-N-(4-nitrophenyl)amino]pyrimidine

Starting compounds: 5-[(4-nitrophenyl)amino]pyrimidine and 4-nitrobenzyl bromide

| Elemental Analysis (for $C_{17}H_{13}N_5O_4$): | | | |
|---|---|---|---|
| | C (%) | H (%) | N (%) |
| Calcd. | 58.12 | 3.78 | 19.93 |
| Found | 58.09 | 3.71 | 19.79 |

NMR Spectrum (DMSO-$d_6$, TMS internal standard) δ: 5.40 (2 H, s), 7.04 (2 H, d, J=9 Hz), 7.66 (2 H, d, J=9 Hz), 8.13 (2 H, d, J=9 Hz), 8.23 (2 H, d, J=9 Hz), 8.97 (2 H, s), 9.10 (1 H, s).

EXAMPLE 4

5-[N-(4-Chlorobenzyl)-N-(4-nitrophenyl)amino]pyrimidine

Starting compounds: 5- [(4-nitrophenyl)amino]pyrimidine and 4-chlorobenzyl chloride Elemental Analysis (for $C_{17}H_{13}N_4ClO_2$):

|  | C (%) | H (%) | N (%) | Cl (%) |
|---|---|---|---|---|
| Calcd. | 59.92 | 3.85 | 16.44 | 10.40 |
| Found | 59.83 | 3.87 | 16.39 | 10.45 |

NMR Spectrum (CDCl$_3$, TMS internal standard) δ: 5.04 (2 H, s), 7.17–7.40 (2 H, m), 8.14 (2 H, d, J=9 Hz), 8.71 (2 H, s), 9.06 (1 H, s)

EXAMPLE 5

5-[N-(4-Fluorobenzyl)-N-(4-nitrophenyl)amino]pyrimidine

Starting compounds: 5-[(4-nitrophenyl)amino]pyrimidine and 4-fluorobenzyl bromide Elemental Analysis (for $C_{17}H_{13}N_4FO_2$):

|  | C (%) | H (%) | N (%) | F (%) |
|---|---|---|---|---|
| Calcd. | 62.96 | 4.04 | 17.28 | 5.86 |
| Found | 63.01 | 4.12 | 17.23 | 5.59 |

NMR Spectrum (CDCl$_3$, TMS internal standard) δ: 5.04 (2 H, s), 6.91 (2 H, d, J=9 Hz), 7.02–7.32 (4 H, 8.14 (2 H, d, J=9 Hz), 8.68 (2 H, s), 9.06 (1 H, s).

EXAMPLE 6

5-[N-(4-Cyanobenzyl)-N-(4-nitrophenyl)amino]pyrimidine

Starting compounds: 5-[(4-nitrophenyl) amino]pyrimidine and α-bromo-p-tolunitrile Elemental Analysis (for $C_{18}H_{13}N_5O_2$):

|  | C (%) | H (%) | N (%) |
|---|---|---|---|
| Calcd. | 65.25 | 3.95 | 21.14 |
| Found | 65.26 | 4.02 | 21.08 |

NMR Spectrum (CDCl$_3$, TMS internal standard) δ: 5.14 (2 H, s), 6.90 (2 H, d, J=9 Hz), 7.41 (2 H, d, J=9 Hz), 7.68 (2 H, d, J=9 Hz), 8.70 (2 H, s), (2 H, d, J=9 Hz), 8.70 (2 H, s), 9.08 (1 H, s)

EXAMPLE 7

5-[N-(4-iodobenzyl)-N-(4-nitrophenyl)amino]pyrimidine

Starting compounds: 5-[(4-nitrophenyl)amino]pyrimidine and 4-iodobenzyl chloride Elemental Analysis (for $C_{17}H_{13}N_4IO_2$):

|  | C (%) | H (%) | N (%) | I (%) |
|---|---|---|---|---|
| Calcd. | 47.24 | 3.03 | 12.96 | 29.36 |
| Found | 47.15 | 3.04 | 12.96 | 29.48 |

NMR Spectrum (CDCl$_3$, TMS internal standard) δ: 5.02 (2 H, s), 6.92 (2 H, d, J=9 Hz), 7.02 (2 H, d, J=9 Hz), 7.69 (2 H, d, J=9 Hz), 8.13 (2 H, d, J=9 Hz), 8.70 (2 H, brs), 9.07 (1 H, brs)

EXAMPLE 8

5-[N-(4-Bromobenzyl)-N-(4-cyanophenyl)amino]pyrimidine

Starting compounds: 5-[(4-cyanophenyl)amino]pyrimidine and 4-bromobenzyl bromide Elemental Analysis (for $C_{18}H_{13}N_4Br$):

|  | C (%) | H (%) | N (%) | Br (%) |
|---|---|---|---|---|
| Calcd. | 59.19 | 3.59 | 15.34 | 21.88 |
| Found | 59.18 | 3.61 | 15.38 | 21.70 |

NMR Spectrum (CDCl$_3$, TMS internal standard) δ: 5.00 (2 H, s), 6.94 (2 H, d, J=9 Hz), 7.09 (2 H, d, J=9 Hz), 7.46 (2 H, d, J=9 Hz), 7.60 (2 H, d, J=9 Hz), 8.63 (2 H, brs), 8.99 (1 H, brs).

EXAMPLE 9

5-[N-(4-Cyanophenyl)-N-(4-fluorobenzyl)amino]pyrimidine

Starting compounds: 5-[(4-cyanophenyl)amino]pyrimidine and 4-fluorobenzyl bromide Elemental Analysis (for $C_{18}H_{13}N_4F$):

|  | C (%) | H (%) | N (%) | F (%) |
|---|---|---|---|---|
| Calcd. | 71.04 | 4.31 | 18.41 | 6.24 |
| Found | 71.12 | 4.35 | 18.25 | 6.24 |

Mass Spectrum (m/z): 304 (M$^+$)

NMR Spectrum (CDCl$_3$, TMS internal standard) δ: 5.01 (2 H, s), 6.86–7.19 (6 H, m), 7.54 (2 H, d, J=9 Hz), 8.64 (2 H, br), 8.99 (1 H, s)

EXAMPLE 10

5-[N-(4-Cyanophenyl)-N-(4trifluoromethyl)benzyl]amino]pyrimidine

Starting compound: 5-[(4-cyanophenyl) amino]pyrimidine and 4-(trifluoromethyl)benzyl bromide Elemental Analysis (for $C_{19}H_{13}N_4F_3$):

|  | C (%) | H (%) | N (%) | F (%) |
|---|---|---|---|---|
| Calcd. | 64.41 | 3.70 | 15.81 | 16.09 |
| Found | 64.46 | 3.75 | 15.91 | 16.05 |

Mass Spectrum (m/z): 354 (M$^+$)

NMR Spectrum (CDCl$_3$, TMS internal standard) δ: 5.10 (2 H, s), 7.12 (2 H, d, J=9 Hz), 7.30–7.70 (6 H, m), 8.65 (2 H, br), 9.01 (1 H, s)

EXAMPLE 11

5-[N-(4-Chlorobenzyl)-N-(4-cyanophenyl)amino]pyrimidine

Starting compounds: 5-[(4-cyanophenyl)amino]pyrimidine and 4-chlorobenzyl chloride Elemental Analysis (for $C_{18}H_{13}N_4Cl$):

|  | C (%) | H (%) | N (%) | Cl (%) |
| --- | --- | --- | --- | --- |
| Calcd. | 67.40 | 4.08 | 17.47 | 11.05 |
| Found | 67.38 | 4.09 | 17.44 | 11.06 |

Mass Spectrum (m/z): 320 ($M^+$)

NMR Spectrum (CDCl$_3$, TMS internal standard) δ: 5.01 (2 H, s), 6.97 (2 H, d, J=9 Hz) , 7.27 (2 H, d, J=9 Hz), 7.34 (2 H, d, J=9 Hz), 7.53 (2 H, d, J=9 Hz), 8.63 (2 H, br), 8,89 (1 H, s),

EXAMPLE 12

5- [N-(4-Cyanophenyl)-N-(4-iodobenzyl)amino]pyriddine

Starting compounds: 5-[(4-cyanophenyl)amino]pyrimidine and 4-iodobenzyl chloride Elemental Analysis (for $C_{18}H_{13}N_4I$):

|  | C (%) | H (%) | N (%) | I (%) |
| --- | --- | --- | --- | --- |
| Calcd. | 52.45 | 3.18 | 13.59 | 30.78 |
| Found | 52.32 | 3.08 | 13.55 | 31.06 |

Mass Spectrum (m/z): 412 ($M^+$)

NMR Spectrum (CDCl$_3$, TMS internal standard) δ: 4.98 (2 H, s), 6.96 (2 H, d, J=9 Hz), 7.01 (2 H, d, J=9 Hz) , 7.53 (2 H, d, J=9 Hz) , 7.68 (2 H, d, J=9 Hz), 8.64 (2 H, br), 9.00 (1 H, s)

EXAMPLE 13

5-[N-(4-Cyanobenzyl)-N-(4-cyanophenyl)amino]pyrimidine

Starting compounds: 5-[(4-cyanophenyl)amino]pyrimidine and α-bromo-p-tolunitrile Elemental Analysis (for $C_{19}H_{13}N_5$):

|  | C (%) | H (%) | N (%) |
| --- | --- | --- | --- |
| Calcd. | 73.30 | 4.21 | 22.49 |
| Found | 73.37 | 4.15 | 22.53 |

Mass Spectrum (m/z): 311 ($M^+$)

NMR Spectrum (CDCl$_3$, TMS internal standard) δ: 5.10 (2 H, s), 6.95 (2 H, d, J=9 Hz), 7.40 (2 H, d, J=8 Hz), 7.55 (2 H, d, J=9 Hz), 7.67 (2 H, d, J=8 Hz), 8.64 (2 H, s), 9.01 (1 H, s).

EXAMPLE 14

5-[N-[(2-Bromopyridin-5-yl)methyl]-N-(4cyanophenyl)amino]pyrimidine

Starting compounds: 5- [(4-Cyanophenyl) amino]pyrimidine and 2-bromo-5-(bromomethyl)pyridine Elemental Analysis (for $C_{17}H_{12}N_5Br$):

|  | C (%) | H (%) | N (%) |
| --- | --- | --- | --- |
| Calcd. | 55.76 | 3.30 | 19.12 |
| Found | 55.12 | 3.24 | 19.08 |

Mass Spectrum (m/z): 365 ($M^+$)

NMR Spectrum (CDCl$_3$, TMS internal standard) δ: 5.02 (2 H, s), 6.95 (2 H, d, J=9 Hz), 7.47 (2 H, s), 7.56 (2 H, d, J=9 Hz) , 8.36 (1 H, s), 8.63 (2 H, br), 9.03 (1 H, s).

EXAMPLE 15

5-[Bis(4-cyanophenyl)amino]pyrimidine

Starting compounds: 5-[(4-cyanophenyl)amino]pyrimidine and 4-fluorobenzonitrile

Elemental Analysis (for $C_{18}H_{11}N_5$):

|  | C (%) | H (%) | N (%) |
| --- | --- | --- | --- |
| Calcd. | 72.72 | 3.78 | 23.56 |
| Found | 72.19 | 3.88 | 23.34 |

Mass Spectrum (m/z): 297 ($M^+$)

NMR Spectrum (CDCl$_3$, TMS internal standard) δ: 7.16 (4, d, J=9 Hz), 7.64 (4 H, d, J=9 Hz), 8.58 (2 H, brs) , 9.05 (1 H, s).

EXAMPLE 16

5-[Bis (4-nitrophenyl) amino]pyrimidine

Starting compounds: 5- [(4-nitrophenyl) amino]pyrimidine and 4-fluoronitrobenzene Elemental Analysis (for $C_{16}H_{11}N_5O_4$):

|  | C (%) | H (%) | N (%) |
| --- | --- | --- | --- |
| Calcd. | 56.98 | 3.29 | 20.76 |
| Found | 56.82 | 3.35 | 20.71 |

Mass Spectrum (m/z): 337 ($M^+$)

NMR Spectrum (DMSO-d$_6$ , TMS internal standard) δ: 7.33 (4 H, d, J=9 Hz), 8.23 (4 H, d, J=9 Hz), 8.78 (2 H, s), 9.12 (1 H, s)

EXAMPLE 17

5-[N-(4-Cyanophenyl)-N-(4-nitrobenzyl)amino]pyrimidine

Starting compounds: 5-[(4-Cyanophenyl)amino]pyrimidine and 4-nitrobenzyl bromide Elemental Analysis (for $C_{18}H_{13}N_5O_2$):

|  | C (%) | H (%) | N (%) |
| --- | --- | --- | --- |
| Calcd. | 65.25 | 3.95 | 21.14 |
| Found | 64.90 | 3.99 | 20.93 |

Mass Spectrum (m/z): 331 ($M^+$)

NMR Spectrum (CDCl$_3$, TMS internal standard) δ: 5.15 (2 H, 6.97 (2 H, d, J=9 Hz), 7.47 (2 H, d, J=9 Hz) , 7.56 (2 H, J=9 Hz), 8.23 (2 H, d, J=9 Hz), 8.66 (2 H, s), 9.03 (1 H,

EXAMPLE 18

3-[N-(4-Bromobenzyl)-N-(4-cyanophenyl)amino]pyridazine Starting compounds: 3-[(4-Cyanophenyl)amino]pyridazine and 4-bromobenzyl bromide Elemental Analysis (for $C_{18}H_{13}N_4Br$):

|  | C (%) | H (%) | N (%) | Br (%) |
|---|---|---|---|---|
| Calcd. | 59.19 | 3.59 | 15.34 | 21.88 |
| Found | 59.16 | 3.63 | 15.28 | 21.70 |

Mass Spectrum (m/z): 365 ($M^+$)

NMR Spectrum (CDCl$_3$, TMS internal standard) δ: 5.37 (2 H, s), 7.03 (1 H, d, J=9 Hz), 7.17 (2 H, d, =8 Hz), 7.28 (2 H, d, J=8 Hz), 7.32 (1 H, br), 7.40 (2 H, J=8 Hz), 7.66 (2 H, d, J=8 Hz), 8.78 (1 H, br)

EXAMPLE 19

2-[N-(4-Bromobenzyl)-N-(4-cyanophenyl)amino]-1,2,4-triazine

Starting compounds: 2-[(4-cyanophenyl)amino-1,2,4-triazine and 4-bromobenzyl bromide Elemental Analysis (for $C_{17}H_{12}N_5Br$):

|  | C (%) | H (%) | N (%) | Br (%) |
|---|---|---|---|---|
| Calcd. | 55.76 | 3.30 | 19.12 | 21.82 |
| Found | 55.63 | 3.37 | 19.21 | 21.97 |

NMR Spectrum (CDCl$_3$, TMS internal standard) δ: 5.32 (2 H, s), 7.13 (2 H, d, J=9 Hz), 7.39 (2 H, d, J=4 Hz), 7.45 (2 H, d, J=4 Hz), 7.68 (2 H, d, J=9 Hz), 8.20 (1 H, d, J=2 Hz), 8.74 (1 H, d, J=2 Hz)

EXAMPLE 20

4'-[N-(4-Bromobenzyl)-N-(pyrimidin-5-yl)amino]acetophenone

Starting compounds: 4'-[N-(pyrimidin-5-yl)amino]acetophenone and 4-bromobenzyl bromide Elemental Analysis (for $C_{19}H_{16}N_3BrO$):

|  | C (%) | H (%) | N (%) |
|---|---|---|---|
| Calcd. | 59.70 | 4.22 | 10.99 |
| Found | 59.65 | 4.25 | 10.76 |

Mass Spectrum (m/z): 383 (M++i)

NMR Spectrum (CDCl$_3$, TMS internal standard) δ: 2.54 (3 H, s), 5.00 (2 H, s), 7.03 (2 H, d, J=9 Hz), 7.14 (2 H, d, J=9 Hz), 7.47 (2 H, d, J=9 Hz), 7.90 (2 H, d, J=9 Hz), 8.59 (2 H, s), 8.92 (1 H, s)

EXAMPLE 21

5-[N,N-Bis(4-methylsulfonylphenyl)amino]pyrimidine

Starting compounds: 5-[N-(4-methylsulfonylphenyl)amino]pyrimidine and 4-fluoro-methanesulfonylbenzene Elemental Analysis (for $C_{18}H_{17}N_3O_4S_2$):

|  | C (%) | H (%) | N (%) | S (%) |
|---|---|---|---|---|
| Calcd. | 53.58 | 4.25 | 10.41 | 15.89 |
| Found | 53.54 | 4.19 | 10.38 | 15.98 |

NMR Spectrum (DMSO-d$_6$, TMS internal standard) δ: 3.21 (6 H, s), 7.32 (4 H, d, J=9 Hz), 7.89 (4 H, d, J=9 Hz), 8.70 (2 H, s), 9.05 (1 H, s)

EXAMPLE 22

5-[N-(4-Bromobenzyl)-N-(4-methylsulfonylphenyl)amino]pyrimidine

Starting compounds: 5-[N-(4-methylsulfonylphenyl)amino]pyrimidine and 4-bromobenzyl bromide Elemental Analysis (for $C_{18}H_{16}N_3BrO_2S$):

|  | C (%) | H (%) | N (%) | Br (%) | S (%) |
|---|---|---|---|---|---|
| Calcd. | 51.68 | 3.86 | 10.05 | 19.10 | 7.67 |
| Found | 51.45 | 3.73 | 9.99 | 18.90 | 7.68 |

NMR Spectrum (CDCl$_3$, TMS internal standard) δ: 3.03 (3 H, s), 5.01 (2 H, s), 7.02 (2 H, d, J=9 Hz), 7.15 (2 H, d, J=9 Hz), 7.48 (2 H, d, J=9 Hz), 7.80 (2 H, d, J=9 Hz), 8.64 (2 H, s), 9.00 (1 H, s)

EXAMPLE 23

5-[N-(4-Cyanophenyl)-N-(4-nitrophenyl)amino]pyrimidine

Starting compounds: 5-[N-(4-cyanophenyl)amino]pyrimidine and 4-fluoronitrobenzene Elemental Analysis (for $C_{17}H_{11}N_5O_2$):

|  | C (%) | H (%) | N (%) |
|---|---|---|---|
| Calcd. | 64.35 | 3.49 | 22.07 |
| Found | 64.21 | 3.49 | 22.08 |

NMR Spectrum (CDCl$_3$, TMS internal standard) δ: 7.15 (2 H, d, J=9 Hz), 7.19 (2 H, d, J=9 Hz), 7.67 (2 H, d, J=9 Hz), 8.21 (2 H, d, J=9 Hz), 8.59 (2 H, s), 9.08 (1 H, s)

EXAMPLE 24

5-[N-(4-Cyanophenyl)-N-(3,4-dichlorobenzyl)amino]pyrimidine

Starting compounds: 5-[N-(4-cyanophenyl)amino]pyrimidine and 3,4-dichlorobenzyl chloride Elemental Analysis (for $C_{18}H_{12}N_4Cl_2$):

|  | C (%) | H (%) | N (%) | Cl (%) |
|---|---|---|---|---|
| Calcd. | 60.86 | 3.40 | 15.77 | 19.96 |
| Found | 60.73 | 3.36 | 15.58 | 19.45 |

NMR Spectrum (CDCl$_3$, TMS internal standard) δ: 4.99 (2 H, s), 6.95 (2 H, d, J=9 Hz), 7.10 (2 H, dd, J=9 Hz, 2 Hz), 7.37 (1 H, d, J=2 Hz), 7.55 (2 H, d, J=9 Hz), 8.63 (2 H, s), 9.01 (1 H, s)

EXAMPLE 25

5- [N-(4-Cyanophenyl)-N-(4-trifluoromethylphenyl)amino]pyrimidine

Starting compounds: 5- [N-(4-cyanophenyl) amino]pyrimidine and 4-fluorobenzotrifluoride

| | Elemental Analysis (for C$_{18}$H$_{11}$N$_4$F$_3$): | | | |
|---|---|---|---|---|
| | C (%) | H (%) | N (%) | F (%) |
| Calcd. | 63.53 | 3.26 | 16.46 | 16.75 |
| Found | 63.45 | 3.27 | 16.49 | 16.64 |

NMR Spectrum (CDCl$_3$, TMS internal standard) δ: 7.07 (2 H, d, J=9 Hz), 7.21 (2 H, d, J=9 Hz), 7.59 (2 H, d, J=9 Hz), 7.62 (2 H, d, J=9 Hz), 8.59 (2 H, s), 9.00 (1 H, s)

EXAMPLE 26

5-[N-[(2-Bromopyridin-5-yl)methyl]-N-(4-cyanophenyl)amino]pyrimidine (110 mg) obtained in Example 14 was dissolved in a small amount of ethyl acetate, and 5 ml of a 4 N hydrochloric acid solution in ethyl acetate was added thereto with stirring. The stirring was continued for several hours. The thus formed hydrochloride was washed with an adequate amount of ethyl acetate to recover 90 mg of pale yellow crystals.

| | Elemental Analysis (for C$_{17}$H$_{12}$N$_5$BrCl): | | |
|---|---|---|---|
| | C (%) | H (%) | N (%) |
| Calcd. | 50.71 | 3.25 | 17.39 |
| Found | 51.12 | 3.24 | 17.16 |

Mass Spectrum (m/z): 365 (M-HCl)$^+$

NMR Spectrum (DMSO-d6, TMS internal standard) δ: 5.19 (2 H, s), 7.06 (2 H, d, J=9 Hz), 7.61–7.71 (4 H, m), 8.38 (1 H, d, J=2 Hz), 8.84 (2 H, s), 8.99 (1 H, s)

EXAMPLE 27

Five milliliters of ethanol was added to a mixture of 0.25 g of 5-[N-(4-cyanophenyl)-N-(4-fluorobenzyl)amino]pyrimidine obtained in Example 9 and 74 mg of oxalic acid, and the mixture was heated to form a solution. Ethanol was removed by distillation, and ethyl ether was added to the residue for crystallization. The crystals were washed with ethyl ether to obtain 100 mg of 5-[N-(4-cyanophenyl)-N-(4-fluorobenzyl)amino]pyrimidine ½ oxalate.

| | Elemental Analysis (for C$_{19}$H$_{14}$N$_4$OF$_2$): | | | |
|---|---|---|---|---|
| | C (%) | H (%) | N (%) | F (%) |
| Calcd. | 65.33 | 4.04 | 16.04 | 5.44 |
| Found | 65.28 | 4.12 | 15.77 | 5.53 |

NMR Spectrum (CDCl$_3$, +DMSO-d$_6$, TMS internal standard) δ: 5.03 (2 H, s), 6.95–7.37 (6 H, m), 7.55 (2 H, d, J=9 Hz), 8.64 (2 H, s), 8.97 (1 H, s)

The compound of Example 28 was obtained in the same manner as in Example 1.

EXAMPLE 28

5-[N-(4-Cyanophenyl)-N-(3,4-difluorobenzyl)amino]pyrimidine

Starting compounds: 5-[N-(4-cyanophenyl)amino]pyrimidine and 3,4-difluorobenzyl bromide

| | Elemental Analysis (for C$_{18}$H$_{12}$N$_4$F$_2$): | | | |
|---|---|---|---|---|
| | C (%) | H (%) | N (%) | F (%) |
| Calcd. | 67.08 | 3.75 | 17.38 | 11.79 |
| Found | 66.96 | 3.73 | 17.31 | 11.76 |

Mass Spectrum (m/z): 322 (M$^+$)

NMR Spectrum (CDCl$_3$, TMS internal standard) δ: 5.00 (2 H, s), 6.99–7.01 (3 H, m), 7.06–7.10 (1 H, m), 7.13–7.19 (1 H, m), 7.56 (2 H, d, J=9 Hz), 8.64 (2 H, brs), 9.00 (1 H, s)

EXAMPLE 29

To a suspension of 0.04 g of sodium hydride (60% in a mineral oil) in 2 ml of N,N-dimethylformamide was added 0.2 g of 5-[N-(4-cyanophenyl)amino]pyrimidine at room temperature, followed by stirring at that temperature for 1 hour. To the solution was added 0.27 g of 3-bromo-4-fluorobenzyl bromide while cooling with ice, and the mixture was stirred at room temperature for 1 hour. The solvent was removed by distillation under reduced pressure, and water was added to the residue, followed by extraction with chloroform. The chloroform layer was washed with water and dried over anhydrous magnesium sulfate. The solvent was distilled off, and the residue was purified by silica gel column chromatography to collect crude crystals from the chloroform eluate. The crude crystals were recrystallized from a mixed solvent of ethyl acetate and ethyl ether to obtain 0.25 g of 5-[N-(3-bromo-4-fluorobenzyl)-N-(4cyanophenyl)amino]pyrimidine.

| | Elemental Analysis (for C$_{18}$H$_{12}$N$_4$BrF): | | | | |
|---|---|---|---|---|---|
| | C (%) | H (%) | N (%) | Br (%) | F (%) |
| Calcd. | 56.42 | 3.16 | 14.62 | 20.85 | 4.96 |
| Found | 56.29 | 3.19 | 14.56 | 20.95 | 4.79 |

NMR Spectrum (CDCl$_3$, TMS internal standard) δ: 4.99 (2 H, s), 6.96 (2 H, d, J=9 Hz), 7.08–7.19 (2 H, m), 7.41–7.52 (1 H, m), 7.55 (2 H, d, J=9 Hz), 8.62 (2 H, s), 9.00 (1 H, s)

The compounds of Examples 30 to 51 were obtained in the same manner as in Example 29.

EXAMPLE 30

5-[N-(3,4-Difluorobenzyl)-N-(5-pyrimidyl)amino]benzo-fuurazan

Starting compounds: 5-[N-(5-pyrimidyl)amino]benzofurazan and 3,4-difluorobenzyl bromide

| Elemental Analysis (for $C_{17}H_{11}N_5F_2$): | | | |
|---|---|---|---|
| | C (%) | H (%) | N (%) | F (%) |
| Calcd. | 60.18 | 3.27 | 20.64 | 11.20 |
| Found | 60.19 | 3.28 | 20.52 | 10.91 |

Mass Spectrum (m/z): 339 ($M^+$)

NMR Spectrum ($CDCl_3$, TMS internal standard) δ: 5.04 (2 H, s), 7.0–7.35 (5 H, m), 7.74 (1 H, d, J=11 Hz), 8.62 (2 H, s), 9.03 (1 H, s)

EXAMPLE 31

5- [N-(4-Cyanophenyl)-N-(5-pyrimidyl) amino]benzofurazan

Starting compounds: 5-[N-(4-cyanophenyl)amino]pyrimidine and 5-fluororobenzofurazan

| Elemental Analysis (for $C_{17}H_{10}N_6O$): | | | |
|---|---|---|---|
| | C (%) | H (%) | N (%) |
| Calcd. | 64.96 | 3.21 | 26.74 |
| Found | 65.02 | 3.27 | 26.63 |

Mass Spectrum (m/z): 314 ($M^+$)

NMR Spectrum ($CDCl_3$, TMS internal standard) δ: 7.20 (2 H, d, J=9 Hz), 7.21–7.32 (2 H, m), 7.68 (2 H, d, J=9 Hz), 7.86 (1 H, dd, J=10 Hz, 1 Hz), 8.61 (2 H, s), 9.09 (1 H, s)

EXAMPLE 32

5-[N-(4-Bromo-3-fluorobenzyl)-N-(4-cyanophenyl)amino]pyrimidine

Starting compounds: 5-[N-(4-cyanophenyl)amino]pyrimidine and 4-bromo-3-fluorobenzyl bromide

| Elemental Analysis (for $C_{18}H_{12}N_4BrF$): | | | | |
|---|---|---|---|---|
| | C (%) | H (%) | N (%) | Br (%) | F (%) |
| Calcd. | 56.42 | 3.16 | 14.62 | 20.85 | 4.96 |
| Found | 56.27 | 3.25 | 14.56 | 20.66 | 4.92 |

NMR Spectrum ($CDCl_3$, TMS internal standard) δ: 4.99 (2 H, s), 6.91–7.10 (4 H, m), 7.45–7.63 (1 H, m) , 7.55 (2 H, d, J=9 Hz), 8.63 (2 H, s), 9.01 (1 H, s)

EXAMPLE 33

5-[[N-(4-Cyanophenyl)-N-(5-pyrimidyl)amino]methyl] benzofurazan

Starting compounds: 5- [N-(4-cyanophenyl) amino]pyrimidine and 5-bromomethylbenzofurazane

| Elemental Analysis (for $C_{18}H_{12}N_6O$): | | |
|---|---|---|
| | C (%) | H (%) | N (%) |
| Calcd. | 65.85 | 3.68 | 25.60 |
| Found | 65.62 | 3.75 | 25.49 |

Mass Spectrum (m/z): 328 ($M^+$)

NMR Spectrum ($CDCl_3$, TMS internal standard) δ: 5.12 (2 H, s), 7.02 (2 H, d, J=9 Hz), 7.33 (1 H, d, =9 Hz) , 7.58 (2 H, d, J=9 Hz), 7.22 (1 H, s), 7.91 (1 H, J=9 Hz) , 8.71 (2 H, s), 9.05 (1 H, s)

EXAMPLE 34

5-[N-(4-Cyanophenyl)-N-(3,5-difluorobenzyl)amino]pyrimidine

Starting compounds: 5-[N-(4-cyanophenyl)amino]pyrimidine and 3,5-difluorobenzyl bromide

| Elemental Analysis (for $C_{18}H_{12}N_4F_2$): | | | |
|---|---|---|---|
| | C (%) | H (%) | N (%) | F (%) |
| Calcd. | 67.08 | 3.75 | 17.38 | 11.79 |
| Found | 67.00 | 3.69 | 17.33 | 11.90 |

Mass Spectrum (m/z): 322 ($M^+$)

NMR Spectrum ($CDCl_3$, TMS internal standard) δ: 5.02 (2 H, s), 6.74–6.81 (3 H, m), 6.98 (2 H, d, J=9 Hz) , 7.56 (2 H, d, J=9 Hz), 8.65 (2 H, s), 9.01 (1 H, s)

EXAMPLE 35

5- [N-(4-Cyanophenyl)-N-(2,4-difluorobenzyl)amino]-pyrimidine

Starting compounds: 5-[N-(4-cyanophenyl)amino]pyrimidine and 2,4-difluorobenzyl bromide

| Elemental Analysis (for $C_{18}H_{12}N_4F_2$): | | | |
|---|---|---|---|
| | C (%) | H (%) | N (%) | F (%) |
| Calcd. | 67.08 | 3.75 | 17.38 | 11.79 |
| Found | 67.06 | 3.79 | 17.37 | 11.77 |

Mass Spectrum (m/z): 322 ($M^+$)

NMR Spectrum ($CDCl_3$, TMS internal standard) δ: 5.02 (2 H, s), 6.80–6.90 (2 H, m), 6.97 (2 H, d, J=9 HZ) , 7.10–7.20 (1 H, m), 7.54 (2 H, d, J=9 Hz), 8.63 (2 H, S) , 9.01 (1 H, s)

EXAMPLE 36

5-[N-(4-Cyanophenyl)-N-[(2-fluoropyridin-5-yl)methyl]amino]pyrimidine

Starting compounds: 5-[N-(4-cyanophenyl) amino]pyrimidine and 5-(bromomethyl)-2-fluoropyridine

| Elemental Analysis (for $C_{17}H_{12}N_5F$): | | | | |
|---|---|---|---|---|
| | C (%) | H (%) | N (%) | F (%) |
| Calcd. | 66.88 | 3.96 | 22.94 | 6.22 |
| Found | 66.84 | 3.92 | 23.01 | 6.10 |

Mass Spectrum (m/z): 305 (M$^+$)

NMR Spectrum (CDCl$_3$, TMS internal standard) δ: 5.06 (2 H, s), 6.89–7.07 (1 H, m), 6.99 (2 H, d, J=9 Hz), 7.56 (2 H, d, J=9 Hz), 7.76 (1 H, dd, J=3 Hz, 9 Hz), 8.17 (1 H, d, J=9 Hz), 8.63 (2 H, s), 9.00 (1 H, s)

EXAMPLE 37

5-[N-(4-Bromobenzyl)-N-(4-trifluoromethylphenyl)amino]pyrimidine oxalate

Starting compounds: 5-[N-(4-trifluoromethylphenyl)amino]pyrimidine and 4-bromobenzyl bromide Mass Spectrum (m/z): 407 (M-1)$^+$ NMR Spectrum (DMSO-d$_6$, TMS internal standard) δ: 5.14 (2 H, s), 7.17 (2 H, d, J=9 Hz), 7.30 (2 H, d, J=9 Hz), 7.50 (2 H, d, J=9 Hz), 7.59 (2 H, d, J=9 Hz), 8.73 (2 H, s), 8.88 (1 H, s)

EXAMPLE 38

5-[N-Benzyl-N-(4-cyanophenyl)amino]pyrimidine

Starting compounds: 5-[N-(4-cyanophenyl)amino]pyrimidine and benzyl bromide

| Elemental Analysis (for $C_{18}H_{14}N_4$): | | | |
|---|---|---|---|
| | C (%) | H (%) | N (%) |
| Calcd. | 75.51 | 4.93 | 19.57 |
| Found | 75.43 | 5.00 | 19.63 |

Mass Spectrum (m/z): 286 (M$^+$)

NMR Spectrum (CDCl$_3$, TMS internal standard) δ: 5.05 (2 H, s), 7.03 (2 H, d, J=9 Hz), 7.19–7.40 (5 H, m), 7.55 (2 H, d, J=9 Hz), 8.65 (2 H, s), 8.97 (1 H, s)

EXAMPLE 39

5-[N-(4-Cyanophenyl)-N-(2-fluorobenzyl)amino]pyrimidine ½ oxalate

Starting compounds: 5-[N-(4-cyanophenyl)amino]pyrimidine and 2-fluorobenzyl bromide

| Elemental Analysis (for $C_{18}H_{13}N_4F\cdot\frac{1}{2}(C_2H_2O_4)$): | | | | |
|---|---|---|---|---|
| | C (%) | H (%) | N (%) | F (%) |
| Calcd. | 65.33 | 4.04 | 16.04 | 5.44 |
| Found | 65.26 | 14.09 | 16.05 | 5.25 |

Mass Spectrum (m/z): 305 (M+H)$^+$

NMR Spectrum (CDCl$_3$, TMS internal standard) δ: 5.18 (s, 2 H), 7.03 (d, 2 H, J=9 Hz), 7.0–7.5 (4 H, m), 7.66 (d, 2 H, J=9 Hz), 8.81 (2 H, s), 8,98 (1 H, s)

EXAMPLE 40

5-[N-(4-Cyanophenyl)-N-(3-fluorobenzyl)amino]pyrimidine ½ oxalate

Starting compounds: 5-[N-(4-cyanophenyl)amino]pyrimidine and 3-fluorobenzyl bromide

| Elemental Analysis (for $C_{18}H_{13}N_4F\cdot\frac{1}{2}(C_2H_2O_4)$): | | | | |
|---|---|---|---|---|
| | C (%) | H (%) | N (%) | F (%) |
| Calcd. | 65.33 | 4.04 | 16.04 | 5.44 |
| Found | 65.12 | 4.07 | 15.91 | 5.34 |

Mass Spectrum (m/z): 305 (M+H)$^+$

NMR Spectrum (CDCl$_3$, TMS internal standard) δ: 5.18 (2 H, s), 7.05 (d, 2 H, J=9 Hz), 7.0–7.4 (4 H, m), 7.65 (d, 2 H, J=9 Hz), 8.82 (2 H, s), 8.97 (1 H, s)

EXAMPLE 41

5-[N-(4-Cyanophenyl)-N-(2,3,4-trifluorobenzyl)amino]pyrimidine

Starting compounds: 5-[N-(4-cyanophenyl)amino]pyrimidine and 2,3,4-trifluorobenzyl bromide

| Elemental Analysis (for $C_{18}H_{11}N_4F_3$): | | | | |
|---|---|---|---|---|
| | C (%) | H (%) | N (%) | F (%) |
| Calcd. | 63.53 | 3.26 | 16.46 | 16.75 |
| Found | 63.57 | 3.23 | 16.55 | 16.47 |

Mass Spectrum (m/z): 340 (M$^+$)

NMR Spectrum (CDCl$_3$, TMS internal standard) δ: 5.05 (2 H, s), 6.94–6.99 (4 H, m), 7.56 (2 H, d, J=9 Hz), 8.63 (2 H, s), 9.02 (1 H, s)

EXAMPLE 42

5-[N-(4-Cyanophenyl)-N-(2,5-difluorophenyl)amino]pyrimidine

Starting compounds: 5-[N-(4-cyanophenyl)amino]pyrimidine and 2,5-difluorobenzyl bromide

| Elemental Analysis (for $C_{18}H_{11}N_4F_2$): | | | | |
|---|---|---|---|---|
| | C (%) | H (%) | N (%) | F (%) |
| Calcd. | 67.08 | 3.75 | 17.38 | 11.79 |
| Found | 67.13 | 3.70 | 17.32 | 11.59 |

Mass Spectrum (m/z): 322 (M$^+$)

NMR Spectrum (CDCl$_3$, TMS internal standard) δ: 5.04 (2 H, s), 6.91–7.01 (4 H, m), 7.05–7.10 (1 H, m), 7.57 (2 H, d, J=9 Hz), 8.65 (2 H, s), 9.02 (1 H, s)

EXAMPLE 43

5-[N-(3,4-Difluorobenzyl)-N-(5-nitro-2-pyridyl)amino]pyrimidine

Starting compounds: 5-[N-(5-nitro-2-pyridyl)amino]pyrimidine and 3,4-difluorobenzyl bromide

| Elemental Analysis (for $C_{16}H_{11}N_5F_2O_2$): | | | | |
|---|---|---|---|---|
| | C (%) | H (%) | N (%) | F (%) |
| Calcd. | 55.98 | 3.23 | 20.40 | 11.07 |
| Found | 55.84 | 3.34 | 20.33 | 11.01 |

Mass Spectrum (m/z): 343 (M$^+$)

NMR Spectrum (CDCl$_3$, TMS internal standard) δ: 5.27 (2 H, s), 6.40 (1 H, d, J=9 Hz), 7.00–7.26 (3 H, m), 8.17 (1 H, dd, J=9 Hz, 3 Hz), 8.67 (2 H, s), 9.16 (1 H, d, J=3 Hz), 9.21 (1 H, s)

EXAMPLE 44

5-[N-(4-Cyanophenyl)-N-(3-fluoro-4-nitrobenzyl)amino]pyrimidine

Starting compounds: 5-[N-(4-cyanophenyl)amino]pyrimidine and 3-fluoro-4-nitrobenzyl bromide

| Elemental Analysis (for $C_{18}H_{12}N_5F_2O_2$): | | | | |
|---|---|---|---|---|
| | C (%) | H (%) | N (%) | F (%) |
| Calcd. | 61.89 | 3.46 | 20.05 | 5.44 |
| Found | 61.71 | 3.49 | 19.95 | 5.28 |

Mass Spectrum (m/z): 349 (M$^+$)

NMR Spectrum (CDCl$_3$, TMS internal standard) δ: 5.11 (2 H, s), 6.96 (2 H, d, J=9 Hz), 7.22–7.26 (2 H, m), 7.58 (2 H, d, J=9 Hz), 8.10 (1 H, m), 8.67 (2 H, s), 9.06 (1 H, s)

EXAMPLE 45

5-[N-[3,5-Bis(1-cyano-1-methylethyl)benzyl]-N-(4-cyanophenyl)amino]pyrimidine

Starting compounds: 5-[N-(4-cyanophenyl)amino]pyrimidine and 3,5-bis(1-cyano-1-methylethyl)benzyl bromide

| Elemental Analysis (for $C_{26}H_{24}N_6$): | | | |
|---|---|---|---|
| | C (%) | H (%) | N (%) |
| Calcd. | 74.26 | 5.75 | 19.99 |
| Found | 74.20 | 5.82 | 19.91 |

Mass Spectrum (m/z): 420 (M$^+$)

NMR Spectrum (CDCl$_3$, TMS internal standard) δ: 1.69 (12 H, s), 5.10 (2 H, s), 7.00 (2 H, d, J=9 Hz), 7.27–7.45 (3 H, m), 7.56 (2 H, d, J=9 Hz), 8.63 (2 H, s), 8.99 (1 H, s)

EXAMPLE 46

5-[N-(2,4,5-Trifluorobenzyl)-N-(4-cyanophenyl)amino]pyrimidine

Starting compounds: 5-[N-(4-cyanophenyl)amino]pyrimidine and 2,4,5-trifluorobenzyl bromide

| Elemental Analysis (for $C_{18}H_{11}N_4F_3$): | | | | |
|---|---|---|---|---|
| | C (%) | H (%) | N (%) | F (%) |
| Calcd. | 63.53 | 3.26 | 16.46 | 16.75 |
| Found | 63.40 | 3.22 | 16.42 | 16.63 |

Mass Spectrum (m/z): 340 (M$^+$)

NMR Spectrum (CDCl$_3$, TMS internal standard) δ: 5.00 (2 H, s), 6.80–7.30 (2 H, m), 7.00 (2 H, d, J=9 Hz), 7.56 (2 H, d, J=9 Hz), 8.62 (2 H, s), 9.03 (1 H, s)

EXAMPLE 47

5-[N-(4-Cyanophenyl)-N-[1-(4-nitrophenyl)ethenyl]amino]pyrimidine

Starting compounds: 5-[N-(4-cyanophenyl)amino]pyrimidine and 1-(4-nitrophenyl)ethyl methanesulfonate

| Elemental Analysis (for $C_{19}H_{13}N_5O_2$): | | | |
|---|---|---|---|
| | C (%) | H (%) | N (%) |
| Calcd. | 66.47 | 3.82 | 20.40 |
| Found | 66.35 | 3.82 | 20.35 |

Mass Spectrum (m/z): 343 (M$^+$)

NMR Spectrum (CDCl$_3$, TMS internal standard) δ: 5.33 (1 H, d, J=1 Hz), 5.73 (1 H, d, J=1 Hz), 7.12 (2 H, d, J=9 Hz), 7.56 (2 H, d, J=9 Hz), 7.66 (2 H, d, J=9 Hz), 8.19 (2 H, d, J=9 Hz), 8.59 (2 H, s), 8.94 (1 H, s)

EXAMPLE 48

5-[N-(4-Cyanophenyl)-N-[1-(4-nitrophenyl)ethyl]amino]pyrimidine

Starting compounds: 5-[N-(4-cyanophenyl)amino]pyrimidine and 1-(1-iodoethyl)-4-nitrobenzene

| Elemental Analysis (for $C_{19}H_{15}N_5O_2$): | | | |
|---|---|---|---|
| | C (%) | H (%) | N (%) |
| Calcd. | 66.08 | 4.38 | 20.28 |
| Found | 66.03 | 4.42 | 20.32 |

Mass Spectrum (m/z): 345 (M$^+$)

NMR Spectrum (CDCl$_3$, TMS internal standard) δ: 1.62 (3 H, d, J=6 Hz), 5.49 (1 H, d, J=6 Hz), 6.79 (2 H, d, J=9 Hz), 7.50 (2 H, d, J=9 Hz), 7.53 (2 H, d, J=9 Hz), 8.23 (2 H, d, J=9 Hz), 8.42 (2 H, s), 9.18 (1 H, s)

EXAMPLE 49

N-(4-Nitrophenyl)-2-phenyl-N-(5-pyrimidyl)acetamide

Starting compounds: 5-[N-(4-nitrophenyl)amino]pyrimidine and phenylacetyl chloride

| Elemental Analysis (for $C_{18}H_{14}N_4O_3$): | | | |
|---|---|---|---|
| | C (%) | H (%) | N (%) |
| Calcd. | 64.67 | 4.22 | 16.76 |
| Found | 64.66 | 4.30 | 16.64 |

Mass Spectrum (m/z): 334 (M$^+$)

NMR Spectrum (CDCl$_3$, TMS internal standard) δ: 3.72 (2 H, s), 7.10–7.03 (1 H, m), 7.26–7.31 (4 H, m), 7.35 (2 H, d, J=9 Hz), 8.26 (2 H, d, J=9 Hz), 8.57 (1 H, s), 9.11 (1 H, s)

EXAMPLE 50

5-[N-(2-Cyanophenyl)-N-(3,4-difluorobenzyl)amino]pyrimidine hydrochloride

Starting compounds: 5-[N-(2-cyanophenyl)amino]pyrimidine and 3,4-difluorobenzyl bromide

| Elemental Analysis (for $C_{19}H_{13}N_4ClF_2$): | | | | | |
|---|---|---|---|---|---|
| | C (%) | H (%) | N (%) | Cl (%) | F (%) |
| Calcd. | 60.26 | 3.65 | 15.62 | 9.88 | 10.59 |
| Found | 60.37 | 3.68 | 15.65 | 9.75 | 10.64 |

Mass Spectrum (m/z): 322 (M$^+$)

NMR Spectrum (CDCl$_3$, TMS internal standard) δ: 5.12 (2 H, s), 6.80 (1 H, brs), 7.26–7.50 (4 H, m), 7.66 (1 H, d, J=7 Hz), 7.79–7.82 (1 H, m), 7.91 (1 H, dd, J=8 Hz, 1 Hz), 8.33 (2 H, s), 8.72 (1 H, s)

EXAMPLE 51

5-[N-(5-Nitro-2-pyridyl)-N-(4-thiazolylmethyl)amino]pyrimidine

Starting compounds: 5-[N-(5-nitro-2-pyridyl)amino]pyrimidine and 4-chloromethylthiazole

| Elemental Analysis (for $C_{13}H_{10}N_6O_2S$): | | | | |
|---|---|---|---|---|
| | C (%) | H (%) | N (%) | S (%) |
| Calcd. | 59.68 | 3.21 | 26.74 | 10.20 |
| Found | 49.32 | 3.19 | 26.63 | 10.32 |

Mass Spectrum (m/z): 314 (M$^+$)

NMR Spectrum (CDCl$_3$, TMS internal standard) δ: 5.39 (2 H, s), 6.51 (1 H, d, J=9 Hz), 7.33 (1 H, s), 8.20 (1 H, dd, J=3 Hz, 9 Hz), 8.78 (1 H, s), 8.84 (2 H, s), 9.12 (1 H, d, J=3 Hz), 9.19 (1 H, s)

The chemical structural formulae of the compounds obtained in the foregoing Reference Examples and Examples are shown in Tables 1 to 15 below.

TABLE 1

| Reference Example No. | Structural Formula |
|---|---|
| 1 | pyrimidin-5-yl—NH—C$_6$H$_4$—CN |
| 2 | pyrimidin-5-yl—NH—C$_6$H$_4$—NO$_2$ |
| 3 | pyridazin-yl—NH—C$_6$H$_4$—CN |
| 4 | pyridazin-yl—NH—C$_6$H$_4$—CN |
| 5 | pyrimidin-5-yl—N(H)—C$_6$H$_4$—COCH$_3$ |

TABLE 2

| Reference Example No. | Structural Formula |
|---|---|
| 6 | pyrimidin-5-yl—N(H)—C$_6$H$_4$—SO$_2$CH$_3$ |
| 7 | pyrimidin-5-yl—NH—benzofurazanyl |
| 8 | pyrimidin-5-yl—NH—(pyridin-2-yl)—NO$_2$ |
| 9 | pyrimidin-5-yl—NH—C$_6$H$_4$(o-CN) |

TABLE 2-continued

| Reference Example No. | Structural Formula |
|---|---|
| 10 | pyrimidin-5-yl-NH-(4-CF₃-phenyl) |

TABLE 3

| Example No. | Structural Formula |
|---|---|
| 1 | pyrimidin-5-yl-N(4-NO₂-phenyl)(4-CF₃-benzyl) |
| 2 | pyrimidin-5-yl-N(4-NO₂-phenyl)(4-Br-benzyl) |
| 3 | pyrimidin-5-yl-N(4-NO₂-phenyl)(4-NO₂-benzyl) |
| 4 | pyrimidin-5-yl-N(4-NO₂-phenyl)(4-Cl-benzyl) |

TABLE 4

| Example No. | Structural Formula |
|---|---|
| 5 | pyrimidin-5-yl-N(4-NO₂-phenyl)(4-F-benzyl) |
| 6 | pyrazin-2-yl-N(4-NO₂-phenyl)(4-CN-benzyl) |
| 7 | pyrazin-2-yl-N(4-NO₂-phenyl)(4-I-benzyl) |
| 8 | pyrazin-2-yl-N(4-CN-phenyl)(4-Br-benzyl) |

TABLE 5

| Example No. | Structural Formula |
|---|---|
| 9 | pyrimidin-5-yl-N(4-CN-phenyl)(4-F-benzyl) |
| 10 | pyrimidin-5-yl-N(4-CN-phenyl)(4-CF₃-benzyl) |
| 11 | pyrimidin-5-yl-N(4-CN-phenyl)(4-Cl-benzyl) |

TABLE 5-continued

| Example No. | Structural Formula |
|---|---|
| 12 | pyrimidin-5-yl-N-(4-cyanophenyl)-N-(4-iodobenzyl)amine |

TABLE 6

| Example No. | Structural Formula |
|---|---|
| 13 | pyrimidin-5-yl-N-(4-cyanophenyl)-N-(4-cyanobenzyl)amine |
| 14 | pyrimidin-5-yl-N-(4-cyanophenyl)-N-((6-bromopyridin-3-yl)methyl)amine |
| 15 | pyrimidin-5-yl-N,N-bis(4-cyanophenyl)amine |
| 16 | pyrimidin-5-yl-N,N-bis(4-nitrophenyl)amine |

TABLE 7

| Example No. | Structural Formula |
|---|---|
| 17 | pyrimidin-5-yl-N-(4-cyanophenyl)-N-(4-nitrobenzyl)amine |
| 18 | pyridazin-3-yl-N-(4-cyanophenyl)-N-(4-bromobenzyl)amine |
| 19 | 1,2,4-triazin-3-yl-N-(4-cyanophenyl)-N-(4-bromobenzyl)amine |
| 20 | pyrimidin-5-yl-N-(4-acetylphenyl)-N-(4-bromobenzyl)amine |

TABLE 8

| Example No. | Structural Formula |
|---|---|
| 21 | pyrimidin-5-yl-N,N-bis(4-methylsulfonylphenyl)amine |
| 22 | pyrimidin-5-yl-N-(4-methylsulfonylphenyl)-N-(4-bromobenzyl)amine |
| 23 | pyrimidin-5-yl-N-(4-cyanophenyl)-N-(4-nitrophenyl)amine |

TABLE 8-continued

| Example No. | Structural Formula |
|---|---|
| 24 | pyrazin-2-yl-N(4-cyanophenyl)(3,4-dichlorobenzyl) |

TABLE 9

| Example No. | Structural Formula |
|---|---|
| 25 | pyrazin-2-yl-N(4-cyanophenyl)(4-trifluoromethylphenyl) |
| 26 | pyrazin-2-yl-N(4-cyanophenyl)((6-bromopyridin-3-yl)methyl) · HCl |
| 27 | pyrimidin-5-yl-N(4-cyanophenyl)(4-fluorobenzyl) · 1/2 COOH–COOH |
| 28 | pyrimidin-5-yl-N(4-cyanophenyl)(3,4-difluorobenzyl) |

TABLE 10

| Example No. | Structural Formula |
|---|---|
| 29 | pyrazin-2-yl-N(4-cyanophenyl)(3-bromo-4-fluorobenzyl) |
| 30 | pyrazin-2-yl-N(benzofurazan-5-yl)(3,4-difluorobenzyl) |
| 31 | pyrazin-2-yl-N(4-cyanophenyl)(benzofurazan-5-yl) |
| 32 | pyrazin-2-yl-N(4-cyanophenyl)(3-fluoro-4-bromobenzyl) |

TABLE 11

| Example No. | Structural Formula |
|---|---|
| 33 | pyrazin-2-yl-N(4-cyanophenyl)(benzofurazan-5-yl) |
| 34 | pyrimidin-5-yl-N(4-cyanophenyl)(3,5-difluorobenzyl) |

TABLE 11-continued
| Example No. | Structural Formula |
|---|---|
| 35 | 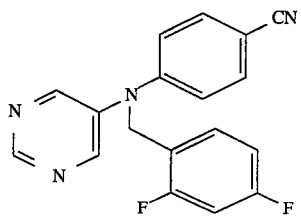 |
| 36 | 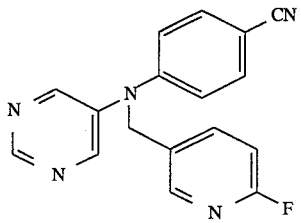 |
TABLE 12
| Example No. | Structural Formula |
|---|---|
| 37 | 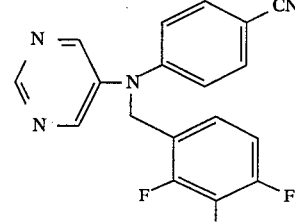 · CO₂H–CO₂H |
| 38 | 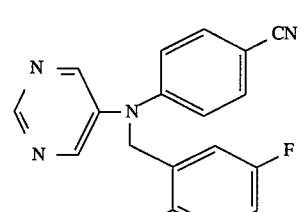 |
| 39 | 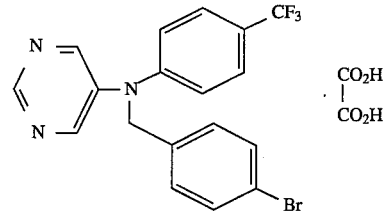 · 1/2 (CO₂H)₂ |
| 40 | 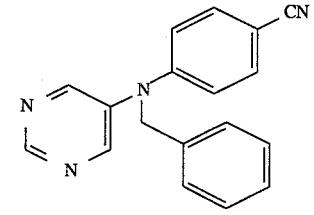 · 1/2 (CO₂H)₂ |
TABLE 13
| Example No. | Structural Formula |
|---|---|
| 41 | 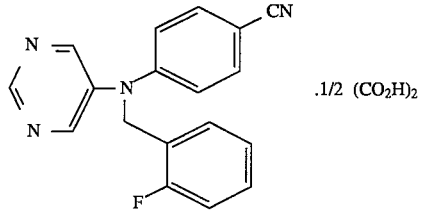 |
| 42 | 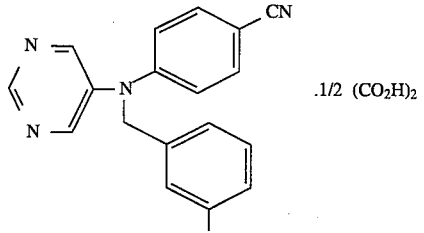 |
| 43 | 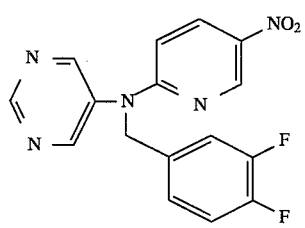 |
| 44 | 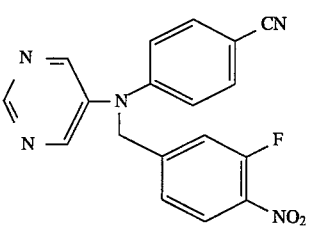 |
TABLE 14
| Example No. | Structural Formula |
|---|---|
| 45 | 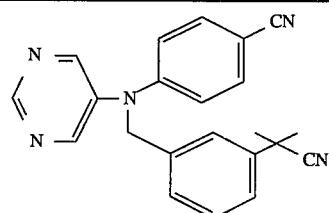 |
| 46 | 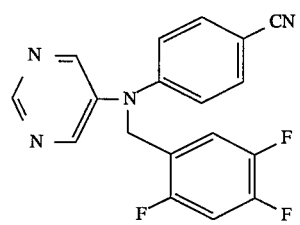 |

TABLE 14-continued

| Example No. | Structural Formula |
|---|---|
| 47 | (pyrazinyl)-N(4-CN-phenyl)(=CH-4-NO₂-phenyl) |
| 48 | (pyrazinyl)-N(4-CN-phenyl)(CH(CH₃)-4-NO₂-phenyl) |

TABLE 15

| Example No. | Structural Formula |
|---|---|
| 49 | (pyrazinyl)-N(4-NO₂-phenyl)-C(=O)-CH₂-phenyl |
| 50 | (pyrazinyl)-N(2-CN-phenyl)(CH₂-3,4-diF-phenyl) · HCl |
| 51 | (pyrazinyl)-N(5-NO₂-pyridin-2-yl)(CH₂-thiazolyl) |

The chemical structural formulae of other compounds of the present invention (Examples A-1 to 30) are shown in Tables 16 to 20 below.

These compounds can easily be synthesized by using the above-described processes, the processes described in the foregoing Examples or modifications thereof according to techniques known to a person having ordinary skill in the art, and no special experimentation is required.

TABLE 16

(I)

| No. | B⟩C— | —C⟨D | —A—C⟨E |
|---|---|---|---|
| 1 | pyrazinyl | 4-CN-phenyl | —(CH₂)₃—(3,5-diF-phenyl) |

TABLE 16-continued
(I)
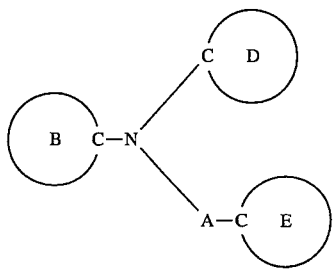
| No. | B⌬C— | —C⌬D | —A—C⌬E |
|---|---|---|---|
| 2 | 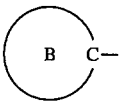 | 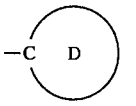 | 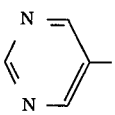 |
| 3 | 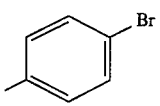 | 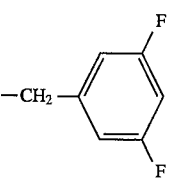 | 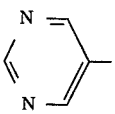 |
| 4 | 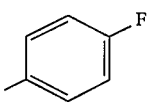 | 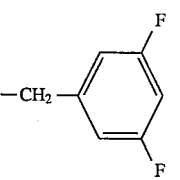 | 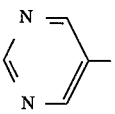 |
| 5 | 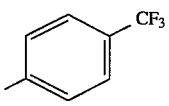 | 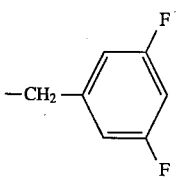 | 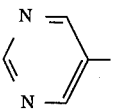 |
| 6 | 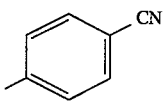 | 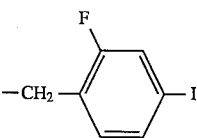 | 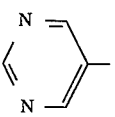 |

TABLE 17

(I)

| No. | B—C⟨ ⟩ | —C⟨D⟩ | —A—C⟨E⟩ |
|---|---|---|---|
| 7 | pyrimidin-5-yl | 4-cyanophenyl | —CH₂—(2,3-dicyanophenyl) |
| 8 | pyrimidin-5-yl | 4-cyanophenyl | —CH₂—(3,5-dichlorophenyl) |
| 9 | pyrimidin-5-yl | 6-pyridyl-3-CN | —CH₂—(3,5-difluorophenyl) |
| 10 | pyrimidin-5-yl | 2-pyrimidinyl-5-CN | —CH₂—(3,5-difluorophenyl) |
| 11 | pyrimidin-5-yl | 5-thienyl-3-CN | —CH₂—(3,5-difluorophenyl) |
| 12 | pyrimidin-5-yl | 5-furyl-3-CN | —CH₂—(3,5-difluorophenyl) |

TABLE 18

(I)

[Structure: B-C-N with branches to C-D and A-C-E]

| No. | B-C- | -C-D | -A-C-E |
|---|---|---|---|
| 13 | pyrimidin-5-yl | 5-cyanothiophen-2-yl (CN on thiophene at 3-position) | -CH₂-(3,5-difluorophenyl) |
| 14 | pyrimidin-5-yl | 4-cyanophenyl | -CH₂-(3,5-dimethylphenyl) |
| 15 | pyrimidin-5-yl | 4-cyanophenyl | -CH₂-(2-fluoro-4-bromophenyl) |
| 16 | pyrimidin-5-yl | 4-cyanophenyl | -CH₂-(2-fluoro-4-trifluoromethylphenyl) |
| 17 | pyrimidin-5-yl | 4-cyanophenyl | -CH₂-(2,3-dinitrophenyl) |
| 18 | pyrimidin-5-yl | 4-cyanophenyl | -CH₂-(2,4-dibromophenyl) |

TABLE 19
(I)
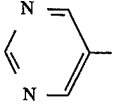
| No. | B⌬C— | —C⌬D | —A—C⌬E |
|---|---|---|---|
| 19 | pyrimidinyl | 4-CN-C₆H₄— | —CH₂—(3-Cl,4-F-C₆H₃) |
| 20 | pyrimidinyl | 4-CN-C₆H₄— | —CH₂—(2,6-Cl₂-C₆H₃) |
| 21 | pyrimidinyl | 4-CN-C₆H₄— | —CH₂—(1-naphthyl) |
| 22 | pyrimidinyl | 4-CN-C₆H₄— | —CH₂—(2-naphthyl) |
| 23 | pyrimidinyl | 4-CN-C₆H₄— | —CH₂—(4-Br-1-naphthyl) |
| 24 | pyrimidinyl | 4-CN-C₆H₄— | —CH₂—(2-Br-thiazol-5-yl) |

TABLE 20

$$\begin{array}{c} B-C-N \begin{array}{c} C-D \\ A-C-E \end{array} \end{array} \quad (I)$$

| No. | B-C- | -C-D | -A-C-E |
|---|---|---|---|
| 25 | pyrazinyl | 4-CN-phenyl | -CH$_2$-benzothiazol-5-yl |
| 26 | pyrazinyl | 4-CN-phenyl | -CH$_2$-(1-methyl-1H-benzotriazol-5-yl) |
| 27 | pyrazinyl | 4-CN-phenyl | -CH$_2$-(1-methyl-1H-benzotriazol-5-yl) (1,3-isomer) |
| 28 | pyrazinyl | 4-CN-phenyl | -CH$_2$-(2-methyl-2H-benzotriazol-5-yl) |
| 29 | pyrazinyl | 4-CN-phenyl | -CH$_2$-quinolin-3-yl |
| 30 | pyrazinyl | 4-CN-phenyl | -CH$_2$-(3,4-dicyanophenyl) |

| Composition: | |
|---|---|
| Core | |
| Compound of Example 34 | 1.0 mg |
| Lactose | 76.4 mg |
| Corn starch | 19.3 mg |
| Hydroxypropylcellulose | 3.0 mg |
| Magnesium stearate | 0.3 mg |
| Sub-total | 100 mg |
| Coat | |
| Hydroxypropylmethylcellulose 2910 | 2.9 mg |
| Polyethylene glycol 6000 | 0.4 mg |
| Titanium oxide | 1.6 mg |
| Talc | 0.1 mg |
| Sub-total | 5 mg |
| Total | 105 mg |

Seven grams of the compound of Example 34 and 534.8 g of lactose were mixed in a polyethylene bag, and the mixture was mixed and ground in a sample mill (manufactured by Hosokawa Micron K.K.). The grinds (541.8 g) and 135.1 g of corn starch were uniformly mixed in a fluidized bed granulating coating machine (manufactured by Ohkawara Seisakusho K.K.), and a 10% solution of 210 g of hydroxypropylcellulose was sprayed thereon to obtain granules. After drying, the granules were passed through a 20 mesh sieve, mixed with 2.1 g of magnesium stearate, and the mixture was made into tablets each weighing 100 mg by means of a rotary tableting machine (manufactured by Hata Tekkojo K.K.) using a pestle of 6.5 mm (diameter)×7.8 R. The resulting tablets were spray-coated with 350 g of a coating solution containing 20.3 g of hydroxypropylmethylcellulose, 2.8 g of polyethylene glycol 6000, 11.2 g of titanium oxide, and 0.7 g of talc to obtain film coated tablets each having a 5 mg coat.

What is claimed is:

1. A substituted tertiary amino compound represented by the general formula (I):

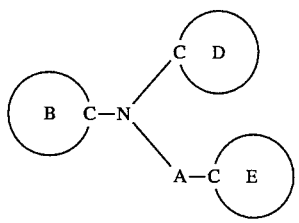

wherein A represents a single bond, a lower alkylene group or a group represented by the formula

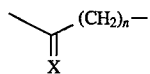

wherein n represents an integer of from 1 to 6, and X represents an oxygen atom, a sulfur atom or a group represented by the formula: $CH_2$;

ring B represents a member selected from the group consisting of a pyrimidine ring;

ring D represents a member selected from the group consisting of (1) an aryl group which is substituted with a cyano group or a nitro group;

(2) a 5- or 6-membered heterocyclic group containing 1 to 3 hetero atoms each selected from a nitrogen atom, an oxygen atom and a sulfur atom, which is substituted with a cyano group or a nitro group; and (3) a bicyclic condensed heterocyclic group consisting of a 5- or 6-membered heterocyclic group containing 1 to 3 hetero atoms each selected from a nitrogen atom, an oxygen atom and a sulfur atom condensed with a benzene ring, and ring E represents a substituted or unsubstituted aryl group, a substituted or unsubstituted 5- or 6-membered heterocyclic group containing 1 to 3 hetero atoms each selected from a nitrogen atom, an oxygen atom, and a sulfur atom, or a substituted or unsubstituted bicyclic condensed heterocyclic group consisting of said heterocylic group condensed with a benzene ring; or a pharmaceutically acceptable salt thereof.

2. A compound as described in claim 1 or a pharmaceutically acceptable salt thereof, wherein said ring D and ring E, which may be the same or different, each represent a benzene ring, a naphthalene ring, an anthracene ring, a phenanthrene ring, a furan ring, a thiophene ring, a thiazole ring, a thiadiazole ring, an oxazole ring, an imidazole ring, a triazole ring, a pyrrole ring, a pyridine ring, a pyrimidine ring, a pyrazine ring, a benzothiazole ring, a benzoxazole ring, a quinoline ring, an isoquinoline ring, a benzotriazole ring or a benzofurazane ring.

3. A compound as described in claim 2 or a pharmaceutically acceptable salt thereof, wherein said ring D and ring E, which may be the same or different, each represent a benzene ring, a pyridine ring, a thiazole ring or a furazane ring.

4. A compound as described in claim 2 or a pharmaceutically acceptable salt thereof, wherein said one or more substituents which are on ring E are, a halogen atom, a cyano group, and a nitro group.

5. A compound as described in claim 1 or a pharmaceutically acceptable salt thereof, wherein A is a lower alkylene group; ring B is a pyrimidine ring; ring D and ring E, which may be the same or different, are each a benzene ring, a pyridine ring, a thiazole ring or a furazane ring; and the substituents on ring E, are a halogen atom, a cyano group, or a nitro group.

6. A compound as described in claim 5 or a pharmaceutically acceptable salt thereof, wherein ring D and ring E are each a benzene ring; and the substituents on ring E are a halogen atom, a cyano group, or a nitro group.

7. 5-[N-(4-Cyanophenyl)-N-(3,5-difluorobenzyl)amino] pyrimidine or a pharmaceutically acceptable salt thereof.

8. A pharmaceutical composition comprising a compound claimed in claim 1 or a pharmaceutically acceptable salt thereof and a pharmaceutically acceptable carrier.

9. An aromatase inhibiting agent comprising a compound claimed in claim 1 or a pharmaceutically acceptable salt thereof as an active ingredient and a pharmaceutically acceptable carrier.

10. An agent for treating breast cancer, mastopathy, endometriosis or prostatic hypertrophy comprising a compound claimed in claim 1 or a pharmaceutically acceptable salt thereof as an active ingredient and a pharmaceutically acceptable carrier.

11. An agent for treating breast cancer or endometriosis comprising a compound claimed in claim 1 or a pharmaceutically acceptable salt thereof as an active ingredient and a pharmaceutically acceptable carrier.

* * * * *